US010959687B2

(12) United States Patent
Yakacki et al.

(10) Patent No.: US 10,959,687 B2
(45) Date of Patent: Mar. 30, 2021

(54) IMAGING TABLE-TO-HEAD FRAME ADAPTER

(71) Applicant: The Regents of the University of Colorado, a body corporate, Denver, CO (US)

(72) Inventors: Christopher Yakacki, Denver, CO (US); Eric J. Losty, Ft. Lupton, CO (US); Sean McDonough, Westminster, CO (US); Aviva Abosch, Englewood, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 754 days.

(21) Appl. No.: 15/211,692

(22) Filed: Jul. 15, 2016

(65) Prior Publication Data

US 2016/0317103 A1    Nov. 3, 2016

Related U.S. Application Data

(63) Continuation of application No. PCT/US2015/011591, filed on Jan. 15, 2015.
(Continued)

(51) Int. Cl.
*A61B 6/04* (2006.01)
*A61B 5/055* (2006.01)
*A61G 13/12* (2006.01)

(52) U.S. Cl.
CPC .......... *A61B 6/0421* (2013.01); *A61B 5/0555* (2013.01); *A61B 6/04* (2013.01); *A61G 13/121* (2013.01); *A61G 2210/50* (2013.01)

(58) Field of Classification Search
CPC ....... A61B 6/0421; A61B 5/0555; A61B 6/04; A61G 13/121; A61G 2210/50
See application file for complete search history.

(56) References Cited

U.S. PATENT DOCUMENTS 3,099,441 A * 7/1963 Ries ...................... A61B 90/14
                                                                    5/637
4,064,401 A * 12/1977 Marden ................ A61B 6/0421
                                                                    5/601
(Continued)

OTHER PUBLICATIONS

International Search Report and Written Opinion for PCT/US15/11591 (filing date Jan. 15, 2015) dated Apr. 7, 2015; Applicant: The Regents of the University of Colorado, A Body Corporate.
(Continued)

*Primary Examiner* — David R Hare
*Assistant Examiner* — Alexis Felix Lopez
(74) *Attorney, Agent, or Firm* — Nicholas Pfeifer; Smith & Hopen, P. A.

(57) ABSTRACT

An adapter to be used to position and restrain a patient's head movement during magnetic resonance imaging (MRI), computed tomography (CT) imaging, positron emission tomography (PET) imaging, X-ray imaging or other imaging or medical procedures. The adapter has a high degree of adjustability and modularity. The adapter can be fitted to a patient quickly and comfortably by offering translational, rotational and height adjustment during the fitting procedure, thereby reducing the overall time for the MRI. The adapter includes a base, one or more attachment members to selectively affix the base to an imaging table, a pair of upwardly extending spaced-apart supports attached to the base, a stabilizer frame rotatably attached to the pair of supports, and a locking mechanism to selectively prevent rotation of the frame attached to the pair of supports.

18 Claims, 20 Drawing Sheets

Related U.S. Application Data

(60) Provisional application No. 61/927,830, filed on Jan. 15, 2014.

(56) References Cited

U.S. PATENT DOCUMENTS

| | | | | |
|---|---|---|---|---|
| 4,256,112 A | * | 3/1981 | Kopf | A61B 6/501 378/208 |
| 4,463,758 A | * | 8/1984 | Patil | A61B 6/501 33/515 |
| 4,465,069 A | * | 8/1984 | Barbier | A61B 6/0421 600/436 |
| 4,592,352 A | * | 6/1986 | Patil | A61B 90/11 5/637 |
| 4,706,665 A | * | 11/1987 | Gouda | A61B 90/11 604/116 |
| 4,884,566 A | * | 12/1989 | Mountz | A61B 90/14 606/130 |
| 5,143,076 A | * | 9/1992 | Hardy | A61N 5/1031 600/407 |
| 5,276,927 A | * | 1/1994 | Day | A61G 13/121 5/601 |
| 5,663,646 A | * | 9/1997 | Kuth | G01R 33/34046 324/318 |
| 5,680,861 A | | 10/1997 | Rohling | |
| 5,817,106 A | * | 10/1998 | Real | A61B 90/11 606/130 |
| 5,971,997 A | * | 10/1999 | Guthrie | A61B 90/11 606/130 |
| 6,584,630 B1 | * | 7/2003 | Dinkler | A61B 6/0442 5/622 |
| 6,594,839 B1 | * | 7/2003 | Papay | A61G 13/12 297/405 |
| 6,684,428 B2 | * | 2/2004 | Grotenhuis | A61B 90/14 5/622 |
| 6,813,788 B2 | * | 11/2004 | Dinkler | A61B 6/04 5/601 |
| 7,017,209 B1 | * | 3/2006 | De Jong | A61B 6/0442 378/20 |
| 7,313,430 B2 | * | 12/2007 | Urquhart | A61B 90/14 600/424 |
| 7,430,773 B2 | * | 10/2008 | Brown | A61B 6/0428 5/601 |
| 7,730,563 B1 | * | 6/2010 | Sklar | A61B 90/14 5/622 |
| 7,706,828 B2 | | 8/2010 | Green et al. | |
| 8,099,150 B2 | * | 1/2012 | Piferi | A61B 5/055 324/318 |
| 8,548,569 B2 | * | 10/2013 | Piferi | G01R 33/34046 600/407 |
| 8,806,679 B2 | * | 8/2014 | Soto | A61G 13/101 5/507.1 |
| 8,893,333 B2 | * | 11/2014 | Soto | A61G 13/101 5/636 |
| 9,216,126 B2 | * | 12/2015 | Schuele | A61G 13/121 |
| 9,808,322 B2 | * | 11/2017 | Del Deo | A61B 17/8085 |
| D810,304 S | * | 2/2018 | Mattiuzzo | D24/184 |
| 2002/0079898 A1 | * | 6/2002 | Van De Spijker | A61B 5/0555 324/318 |
| 2005/0066444 A1 | * | 3/2005 | Mazzei | A61G 13/12 5/638 |
| 2006/0293589 A1 | * | 12/2006 | Calderon | A61G 7/1019 600/415 |
| 2009/0088627 A1 | * | 4/2009 | Piferi | A61B 5/055 600/422 |
| 2009/0154654 A1 | * | 6/2009 | Holthe | A61B 6/04 378/205 |
| 2010/0059064 A1 | * | 3/2010 | Schule | A61B 90/14 128/845 |
| 2010/0185198 A1 | * | 7/2010 | Piferi | G01R 33/34046 606/54 |
| 2011/0119829 A1 | * | 5/2011 | Skripps | A61B 6/0421 5/601 |
| 2011/0160727 A1 | * | 6/2011 | Arn | A61B 90/14 606/59 |
| 2011/0170671 A1 | * | 7/2011 | Blyakher | A61B 6/0421 378/209 |
| 2011/0226260 A1 | * | 9/2011 | Eder | A61B 5/0555 128/845 |
| 2012/0124748 A1 | * | 5/2012 | Soto | A61G 13/101 5/640 |
| 2012/0260429 A1 | * | 10/2012 | Rolfes | A61G 13/101 5/637 |
| 2013/0019877 A1 | | 1/2013 | Sklar | |
| 2013/0023756 A1 | * | 1/2013 | Driemel | G01R 33/28 600/422 |
| 2014/0079182 A1 | * | 3/2014 | Rouderques | A61B 6/501 378/41 |
| 2014/0096322 A1 | * | 4/2014 | Farag | A61G 13/121 5/622 |
| 2014/0115786 A1 | * | 5/2014 | Wilson | A61G 13/121 5/622 |
| 2014/0116450 A1 | * | 5/2014 | Li | A61G 13/1205 128/876 |
| 2015/0119902 A1 | * | 4/2015 | Rurling | A61B 90/14 606/130 |
| 2015/0238117 A1 | * | 8/2015 | Fielder | A61B 5/0555 5/637 |

OTHER PUBLICATIONS

International Preliminary Report on Patentability for PCT/US2015/011591 (filing date Jan. 15, 2015) dated Jan. 15, 2014; Applicant: The Regents of the University of Colorado, A Body Corporate et al.

Safaee et al., Techniques for the Application of Stereotactic Head Frames Based on a 25-Year Experience. Cureus. 2016. vol. 8 (No. 3): e543.

* cited by examiner

IMAGING TABLE-TO-HEAD FRAME ADAPTER

CROSS-REFERENCE TO RELATED APPLICATIONS

This application is a continuation of International Patent Application No. PCT/US2015/011591, filed Jan. 15, 2015, which claims the benefit of U.S. Provisional Patent Application No. 61/927,830, filed Jan. 15, 2014.

BACKGROUND OF THE INVENTION

1. Field of Invention

This invention relates to medical imaging apparatuses. More specifically, this invention relates to devices that fix the position of a subject's head for medical imaging.

2. Brief Description of the Related Art

Medical imaging procedures often require a subject to be placed in a certain position and remain still during the procedure to accurately capture a desired image. Typically, the subject lays flat on a table to be scanned by computed tomography (CT), magnetic resonance (MR) imaging, positron emission tomography (PET), etc., and the images are acquired. The subject must often remain still for an extended period of time while the image is acquired. Remaining still and in the proper position can be difficult enough for most subjects, but the process becomes far more complicated when the subject suffers from a condition causing tremors or other uncontrolled movement, such as Parkinson's disease.

Systems have been developed to prevent movement of a subject's head during imaging. These systems take a one-size-fits-all approach allowing no capability to tailor the subject's head position. This can put the subject in an awkward or uncomfortable position, which further increases the tension and anxiety of the procedure. In addition, the practitioner or technician may need to tailor the position of the subject to achieve the desired field of view.

Currently there is a need for an adjustable subject-positioning device that allows the subject to be oriented in a selected position, especially one that is comfortable for the subject, such that images may be acquired of the patient in that position. Such a device would greatly increase patient comfort during imaging procedures, while simultaneously reducing anxiety. In addition the device would simplify the imaging technician's job by ensuring that they are able to properly position the subject to facilitate capturing the desired image. This invention serves these important needs as will become apparent in the following disclosure.

BRIEF SUMMARY OF THE INVENTION

The long-standing but heretofore unfulfilled need for is now met by a new, useful, and nonobvious imaging table-to-head frame stabilizer for holding the head of a patient in a selected position during a medical procedure. In a first aspect the novel imaging table-to-head frame stabilizer includes a base, an attachment member connected to the base, a pair of upwardly extending spaced-apart supports also attached to the base, a stabilizer frame rotatably attached to the pair of supports, and a locking mechanism. The attachment member selectively affixes the stabilizer to an imaging table. The stabilizer frame provides an attachment position for a head frame used to secure the head of a subject during an imaging procedure. The locking mechanism selectively prevents the rotation of the stabilizer frame attached to the pair of supports.

The imaging table-to-head frame stabilizer according to the first aspect can have a stabilizer frame that provides a plurality of attachment positions for a head frame. For example, the stabilizer frame could have a horizontal slot to allow the attachment of a head frame within the range of positions defined by the slot. In addition, the attachment positions for the head frame on the stabilizer frame could be a plurality of slots configured to securely engagement the head frame in a plurality of user selected locations on the frame. This would also facilitate the height adjustment of the head frame.

In further embodiments of the imaging table-to-head frame stabilizer according to the first aspect, the attachments members can be clamps that slidingly engage the imaging table. The clamps may then allow the stabilizer to be adjusted in a fore-aft direction along the table and locked thereto.

The attachments members according to the first aspect can be adapted to affix the stabilizer to a variety of tables including a magnetic resonance imaging (MRI) table, a computed tomography (CT) imaging table, positron emission tomography (PET) imaging table, and an X-ray imaging table.

The imaging table-to-head frame stabilizer according to the first aspect can include a fore-aft adjustment member disposed between the attachment member and the base. The fore-aft adjustment member can be used to facilitate the positioning of the base relative to the attachment member. The fore-aft adjustment member can include a first unit coupled to the attachment member and a second unit slidingly engaged to the first unit and coupled to the base and a locking mechanism connected to one of the units and adapted to selectively lock the fore-aft adjustment member.

In a second aspect the present invention provides an imaging table-to-head frame stabilizer that includes a base, an attachment member connected to the base to affix the base to an imaging table, a fore-aft adjustment member disposed between the attachment member and the base, a pair of upwardly extending spaced-apart supports attached to the base, a stabilizer frame rotatably attached to the pair of supports, and a locking mechanism to selectively prevent rotation of the stabilizer frame attached to the pair of supports. The fore-aft adjustment member facilitates positioning of the base relative to the attachment member, while the stabilizer frame provides an attachment position for a head frame that is used to secure the head of a subject during an imaging procedure. The fore-aft adjustment member can include a first unit coupled to the attachment member and a second unit slidingly engaged to the first unit and coupled to the base and a locking mechanism connected to one of the units and adapted to selectively lock the fore-aft adjustment member.

The imaging table-to-head frame stabilizer according to the second aspect can have a stabilizer frame that provides a plurality of attachment positions for a head frame. For example, the stabilizer frame could have a horizontal slot to allow the attachment of a head frame within the range of positions defined by the slot. In addition, the attachment positions for the head frame on the stabilizer frame could be a plurality of slots configured to securely engagement the head frame in a plurality of user selected locations on the frame. This would also facilitate the height adjustment of the head frame.

In further embodiments of the imaging table-to-head frame stabilizer according to the second aspect, the attachments members can be clamps that slidingly engage the imaging table. The clamps may then allow the stabilizer to be adjusted in a fore-aft direction along the table and locked thereto.

The attachments members according to the second aspect can be adapted to affix the stabilizer to a variety of tables including a magnetic resonance imaging (MRI) table, a computed tomography (CT) imaging table, positron emission tomography (PET) imaging table, and an X-ray imaging table.

In a third aspect the present invention provides an imaging table-to-head frame stabilizer that includes a pair of upwardly extending spaced-apart supports to secure the stabilizer to an imaging table, a stabilizer frame rotatably and slidingly attached to the pair of supports, a locking mechanism to selectively prevent rotation of the frame attached to the pair of supports, a locking mechanism to selectively lock the height of the frame slidingly attached to the pair of supports, and a locking mechanism to selectively adjust the horizontal disposition of the stabilizer frame with respect to the imaging table. The stabilizer frame provides an attachment position for a head frame used to secure the head of a subject during imaging. Slidingly attaching the stabilizer frame to the supports enables a user to adjust the height of the frame.

The imaging table-to-head frame stabilizer according to the third aspect can have a stabilizer frame that provides a plurality of attachment positions for a head frame. For example, the stabilizer frame could have a horizontal slot to allow the attachment of a head frame within the range of positions defined by the slot. In addition, the attachment positions for the head frame on the stabilizer frame could be a plurality of slots configured to securely engagement the head frame in a plurality of user selected locations on the frame. This would also facilitate the height adjustment of the head frame.

In further embodiments of the imaging table-to-head frame stabilizer according to the third aspect, the upwardly extending spaced-apart supports can include a clamp to lock the stabilizer to an imaging table. In still further embodiments the clamps can be adapted to slidingly engage the imaging table, such as through grooves integral to the imaging table, thereby allowing the stabilizer to be adjusted in a fore-aft direction along the table and locked thereto. The clamps according to the third aspect can be adapted to affix the stabilizer to a variety of tables including a magnetic resonance imaging (MRI) table, a computed tomography (CT) imaging table, positron emission tomography (PET) imaging table, and an X-ray imaging table.

The imaging table-to-head frame stabilizer according to the third aspect can include a fore-aft adjustment member disposed between the clamp and the stabilizer frame. The fore-aft adjustment member can be used to facilitate the positioning of the stabilizer frame relative to the clamp.

In a fourth aspect the present invention provides an imaging table-to-head frame stabilizer that includes a pair of upwardly extending spaced-apart supports to secure the stabilizer to an imaging table, a stabilizer frame rotatably attached to the pair of supports, a locking mechanism to selectively prevent rotation of the frame attached to the pair of supports, and a locking mechanism to selectively adjust the horizontal disposition of the stabilizer frame with respect to the imaging table. The stabilizer frame provides an attachment position for a head frame used to secure the head of a subject during imaging.

The imaging table-to-head frame stabilizer according to the fourth aspect can have a stabilizer frame that provides a plurality of attachment positions for a head frame. For example, the stabilizer frame could have a horizontal slot to allow the attachment of a head frame within the range of positions defined by the slot. In addition, the attachment positions for the head frame on the stabilizer frame could be a plurality of slots configured to securely engagement the head frame in a plurality of user selected locations on the frame. This would also facilitate the height adjustment of the head frame.

In further embodiments of the imaging table-to-head frame stabilizer according to the fourth aspect, the upwardly extending spaced-apart supports can include a clamp to lock the stabilizer to an imaging table. In still further embodiments the clamps can be adapted to slidingly engage the imaging table, such as through grooves integral to the imaging table, thereby allowing the stabilizer to be adjusted in a fore-aft direction along the table and locked thereto. The clamps according to the fourth aspect can be adapted to affix the stabilizer to a variety of tables including a magnetic resonance imaging (MRI) table, a computed tomography (CT) imaging table, positron emission tomography (PET) imaging table, and an X-ray imaging table.

The imaging table-to-head frame stabilizer according to the fourth aspect can include a fore-aft adjustment member disposed between the clamp and the stabilizer frame. The fore-aft adjustment member can be used to facilitate the positioning of the stabilizer frame relative to the clamp.

BRIEF DESCRIPTION OF THE DRAWINGS

For a fuller understanding of the invention, reference should be made to the following detailed description, taken in connection with the accompanying drawings, in which:

FIG. 23a illustrates the horizontal adjustment of the adapter with the adapter moved forward in the horizontal plane.

FIG. 23b illustrates the horizontal adjustment of the adapter with the adapter moved backward in the horizontal plane.

FIG. 24a illustrates the rotational adjustment of the adapter with the adapter in an upright position.

FIG. 24b illustrates the rotational adjustment of the adapter with the adapter rotated forward.

FIG. 25a illustrates the vertical adjustment of the adapter with the adapter raised in the vertical plane.

FIG. 25b illustrates the vertical adjustment of the adapter with the adapter lowered in the vertical plane.

DETAILED DESCRIPTION OF THE PREFERRED EMBODIMENT

The invention is a new adapter to be used to position and restrain a patient's head movement during magnetic resonance imaging (MRI), computed tomography (CT) imaging, positron emission tomography (PET) imaging, X-ray imaging or other imaging or medical procedures. Currently, deep brain stimulation (DBS) is a standard treatment for movement disorders, such as Parkinson's disease. For DBS to be successful, an electrode must be placed at a precise location in the brain, which is typically smaller than 1 cm. in diameter. To reach this location accurately, stereotaxy is performed to map the 3-dimensional space of the patient's brain. A patient must wear a head frame with radiographic markers during computed tomography (CT) and MRI scans for stereotaxy to be performed. However, when patients suffer from uncontrollable tremors, such as from Parkinson's disease, the movements can disrupt the imaging process and prevent accurate images from being obtained.

Figure 11:
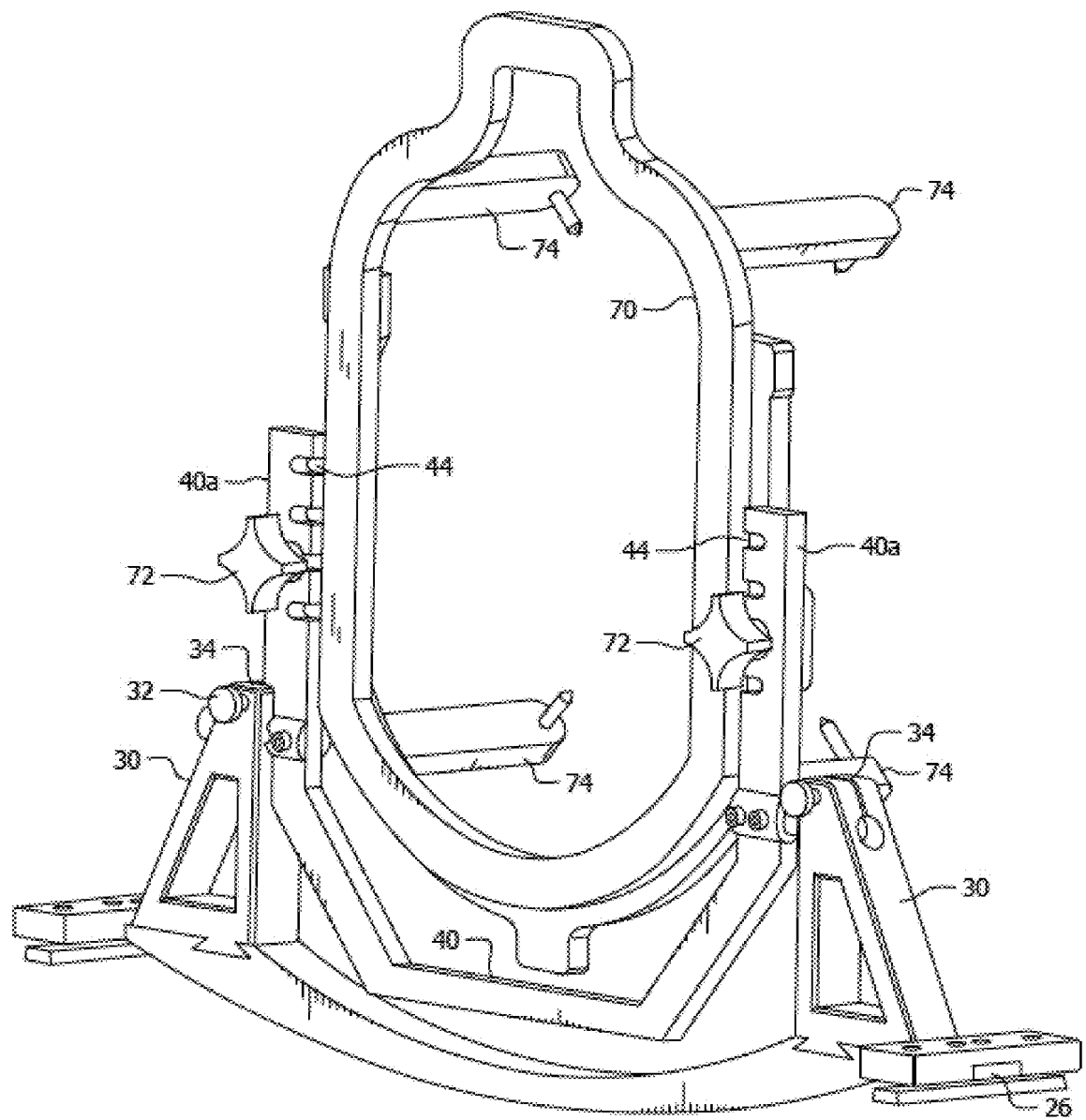
FIG. 11 is a perspective view of the front side of the imaging table-to-head frame adapter shown in FIG. 9 with a head frame attached thereto.
Figure 12:
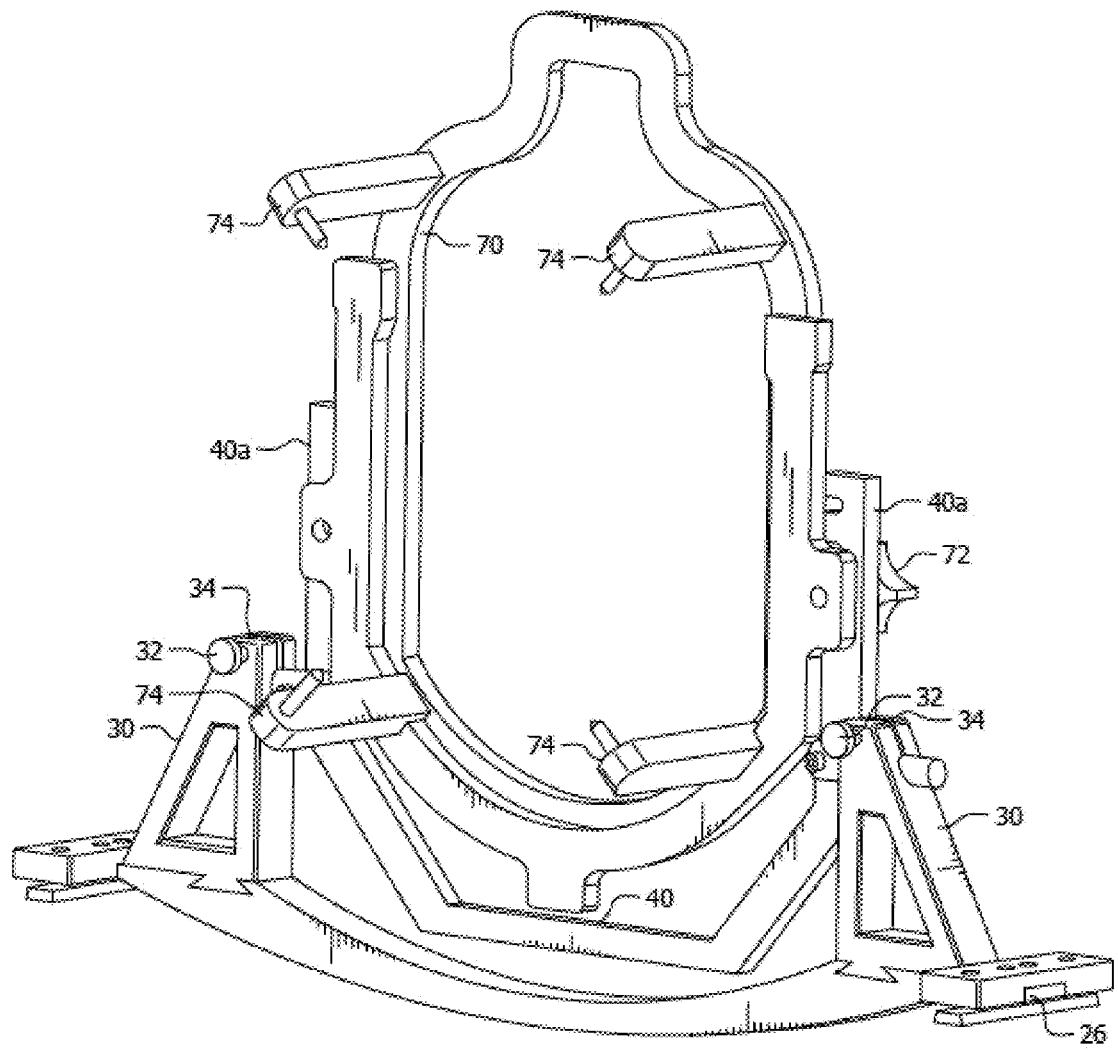
FIG. 12 is a perspective view of the backside of the imaging table-to-head frame adapter shown in FIG. 9 with a head frame attached thereto.
Figure 13:
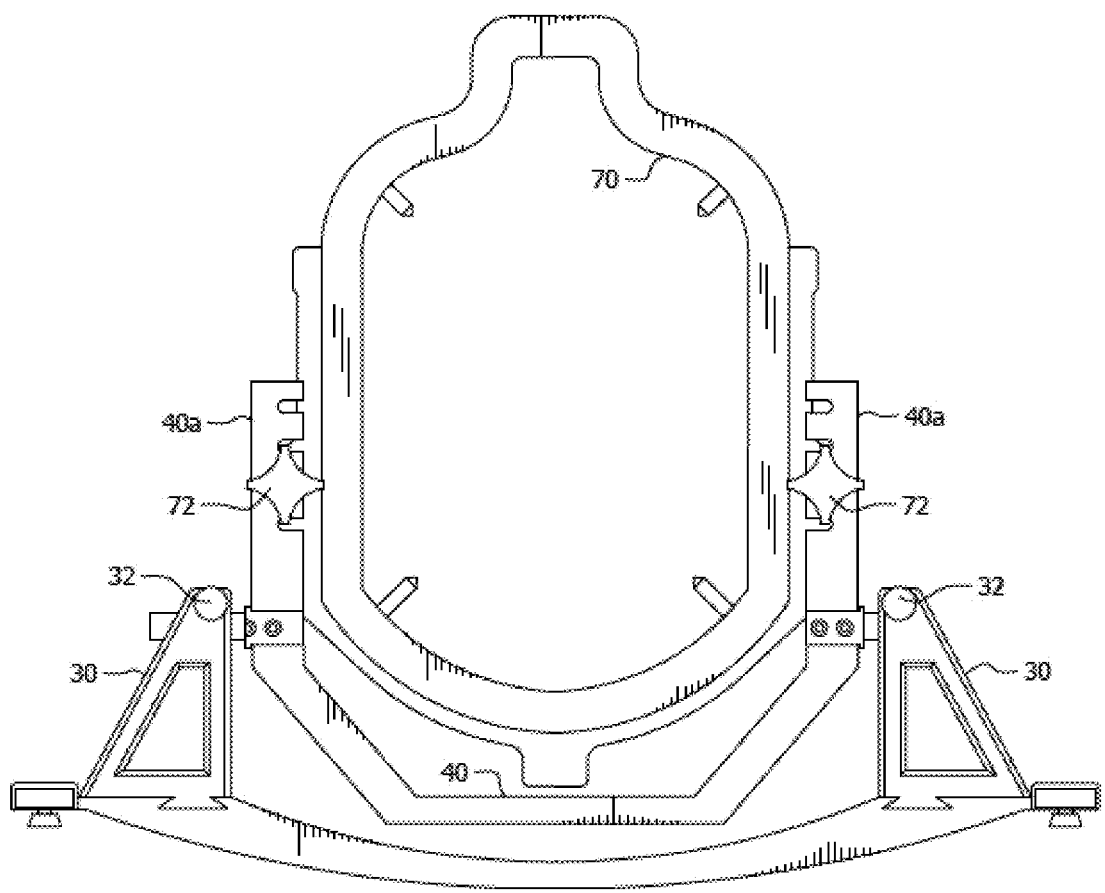
FIG. 13 is a front elevation view of the "imaging table-to-head frame adapter" shown in FIG. 9 with a head frame attached thereto.
Figure 14:
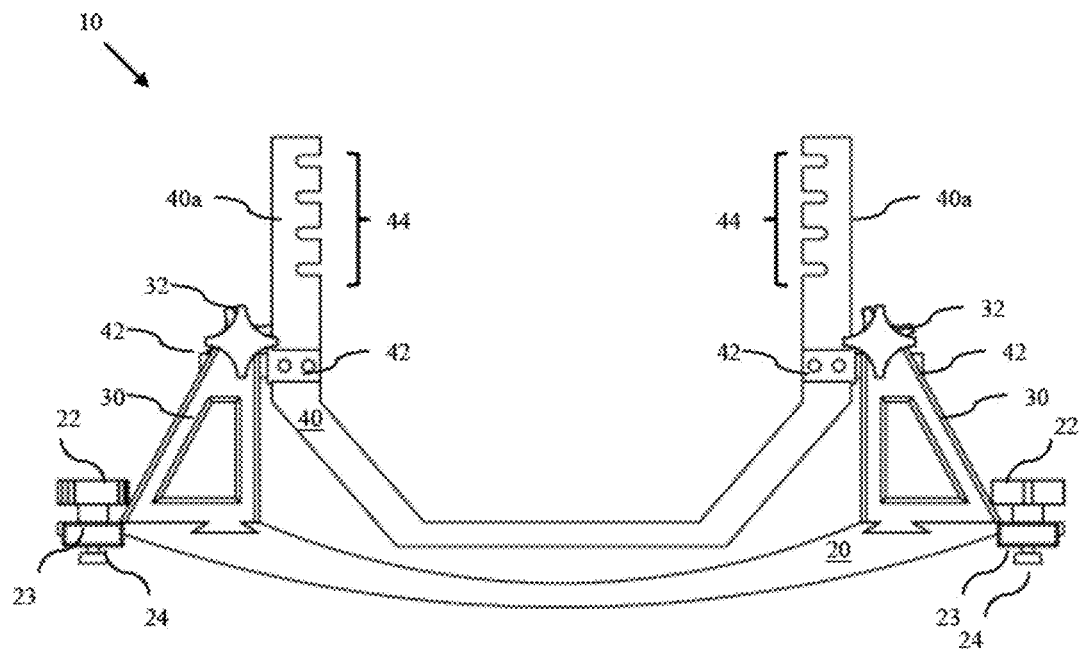
FIG. 14 is a front elevation view of the "imaging table-to-head frame adapter" shown in FIG. 9.
Figure 15:
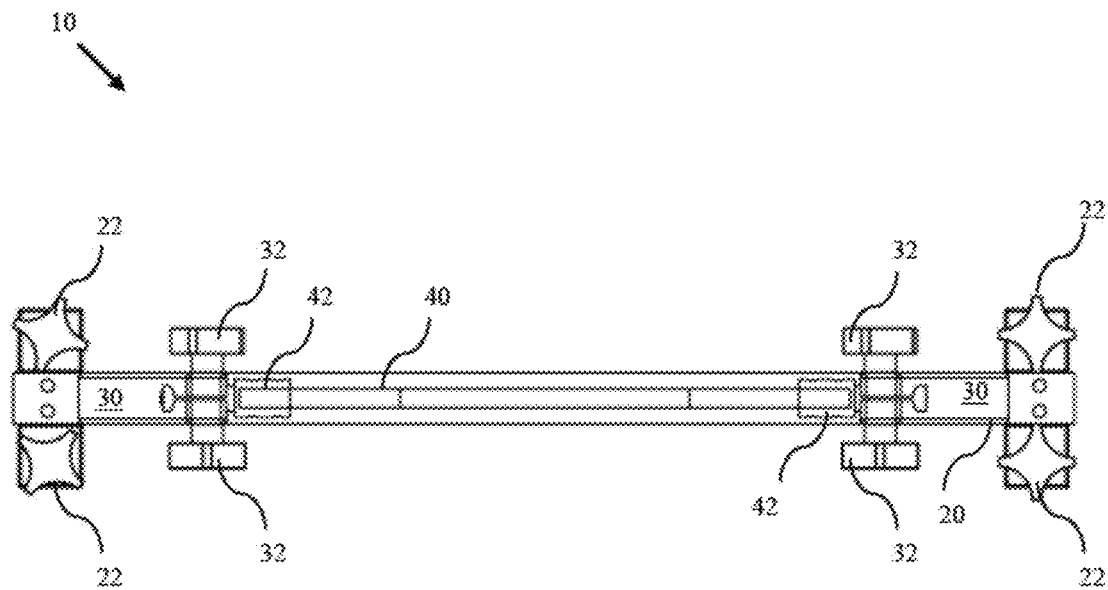
FIG. 15 is a top plan view of the imaging table-to-head frame adapter shown in FIG. 9.
Figure 16:
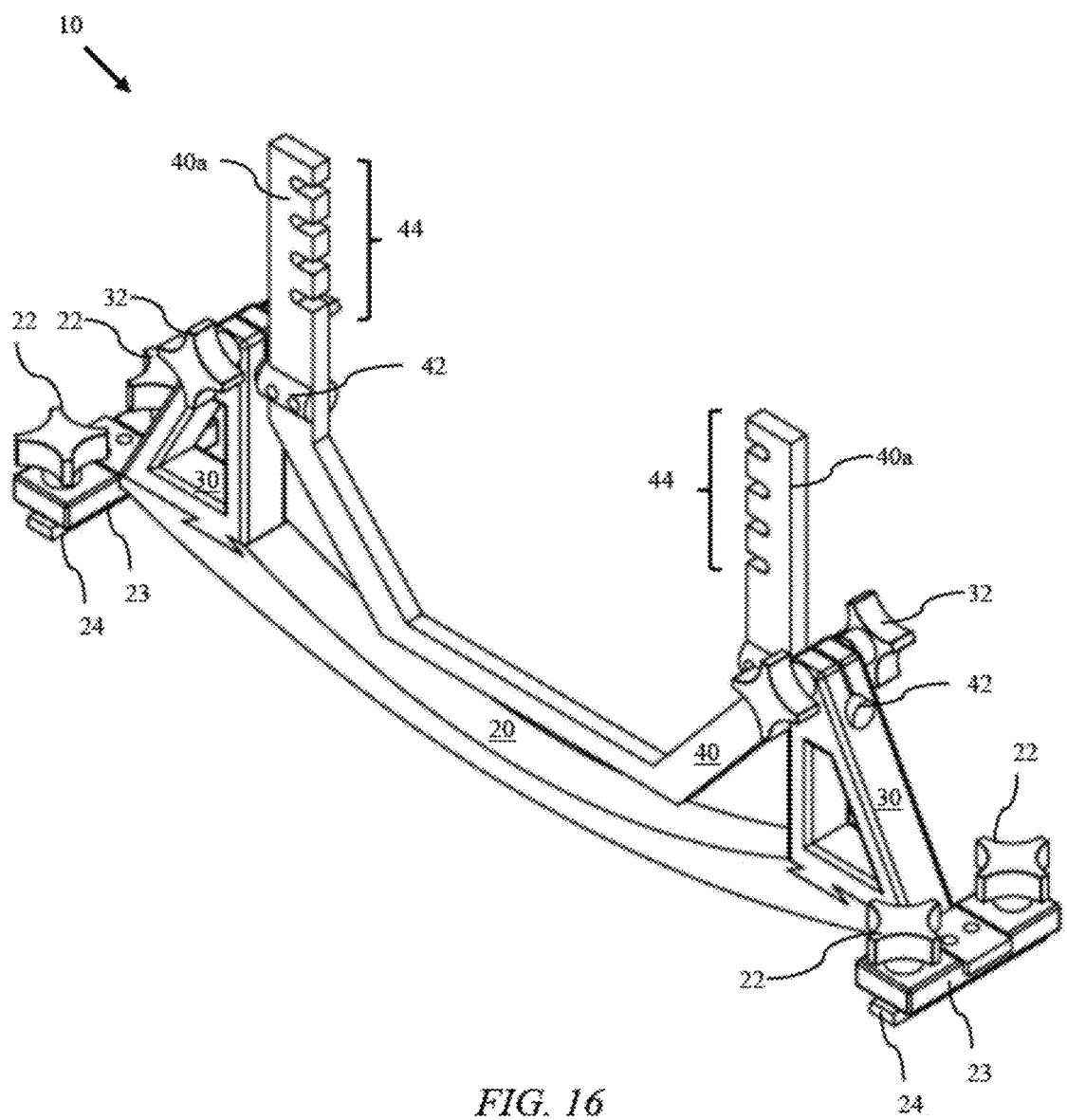
FIG. 16 is a perspective view of the imaging table-to-head frame adapter shown in FIG. 9.
Figure 17:
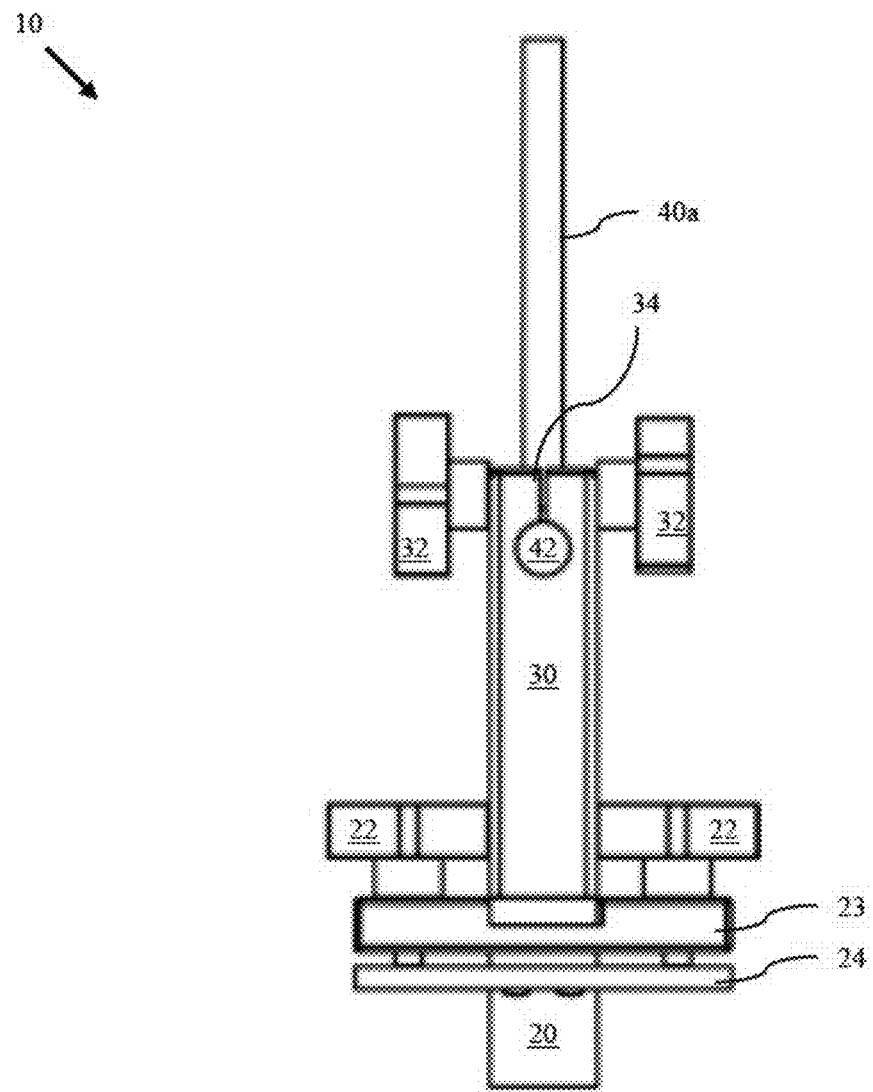
FIG. 17 is a side elevation view of the imaging table-to-head frame adapter shown in FIG. 9.

The present invention prevents the patient from moving their head during MRI or other imaging procedures. By interfacing with the MRI table, the adapter provides a stable constraint to enable MRI for patients who suffer from uncontrollable tremors. The adapter is mounted to an imaging table and a head frame is then mounted to the adapter. A patient's head can then be secured within the head frame. The adapter provides a wide range of adjustments to alter the position of the head frame with respect to the imaging table. FIGS. 11 and 12 show typical head frames used for imaging. A patient's head is secured against the four pins 74 extending from the head frame 70. As can easily be imagined, having one's head locked in place by such pins can be uncomfortable, and this discomfort can be made much worse by having the patient's head in an awkward or contorted position. Also, achieving an additional degree of comfort can help to alleviate some of the associated anxiety resulting from the procedure. Ultimately, the adapter leads to successful stereotaxy and better out comes of DBS.

The adapter has a high degree of adjustability and modularity. The adapter can be fitted to accommodate a patient quickly and comfortably by offering both translational (i.e. along the length of the table), vertical/height (i.e. raising or lowering the patient's head relative to the table) and rotational adjustment (i.e. moving the patient's head as in a nodding motion) during the fitting procedure, thereby reducing the overall time for the MRI. Furthermore, the modular design can be adapted to quickly interface with different MRI tables and stereotaxy frames. In the absence of a design such as that taught herein, if the patient isn't in the perfect position, the patient generally has to sit up again, and the imaging tech make adjustments to the devices, while modifying the positions of the patient's body. The patient then must lie flat again to fit into the frame. This can take multiple tries, a lot of time, and be frustrating for the tech and hard on the patient.

The example below is described for the purposes of explaining the adapter's features primarily in connection with magnetic resonance imaging, which is a preferred embodiment of the present invention. However, the present invention may also be equally applied to other medical imaging systems. For example, the present modular patient handling system may be used in connection with ultrasound, computed tomography (CT), x-ray imaging or positron emission tomography (PET).

Figure 1:
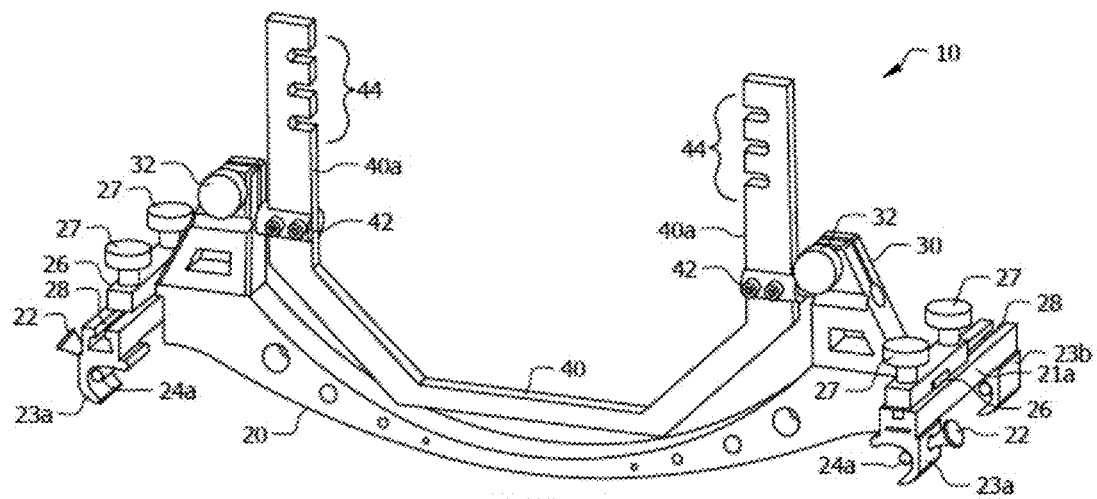
FIG. 1 is a perspective view of the front side, or first side, of an "imaging table-to-head frame adapter," also referred to herein as a "head fixation stabilizer" or simply "adapter", according to some embodiments of the present invention.

Embodiments of the present invention will now be described in detail below with reference to the figures. Referring first to FIG. 1, a head fixation stabilizer 10, also referred to herein as an "imaging table-to-head frame adapter" or simply "adapter", is illustrated. The illustrated head fixation stabilizer 10 includes a base 20 with a pair of imaging table attachment members 21 to affix the head fixation stabilizer 10 to an imaging table. The head fixation stabilizer/adapter 10 is configured to be removably secured to an imaging table using the imaging table attachment members 21. In the illustrated embodiment, the head fixation stabilizer/adapter 10 includes first and second table attachment member 21a and 21b at opposing ends of the base 20.

Figure 2:
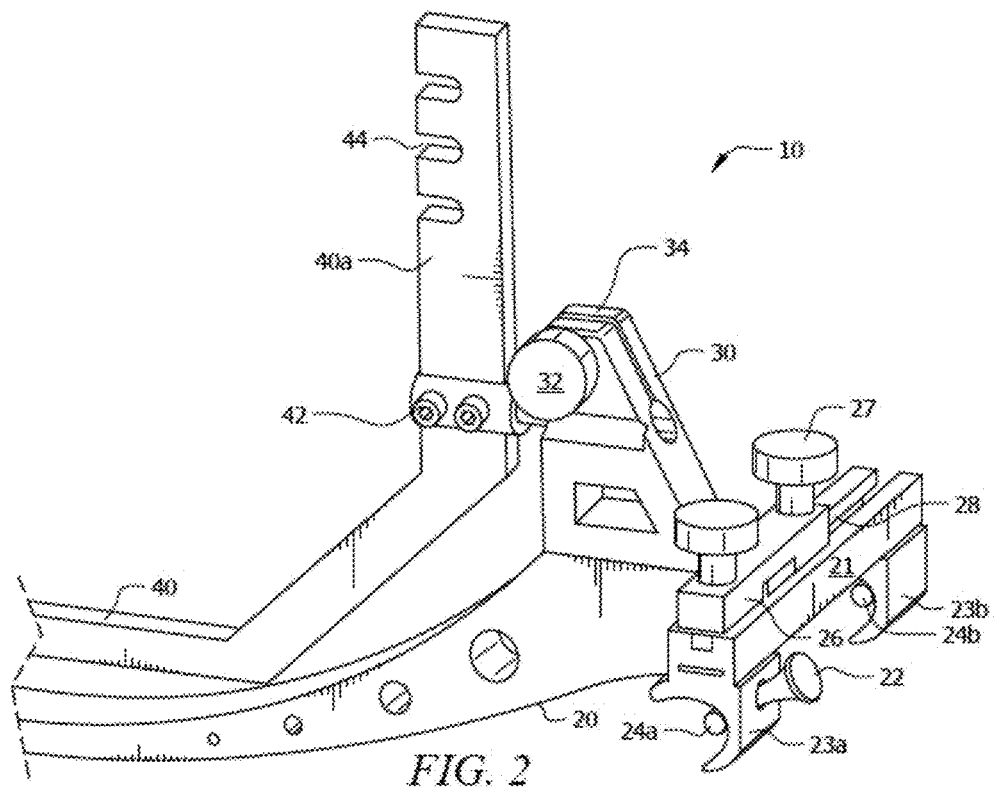
FIG. 2 is a perspective view of the outside right half of the front side of the imaging table-to-head frame adapter shown in FIG. 1.
Figure 4:
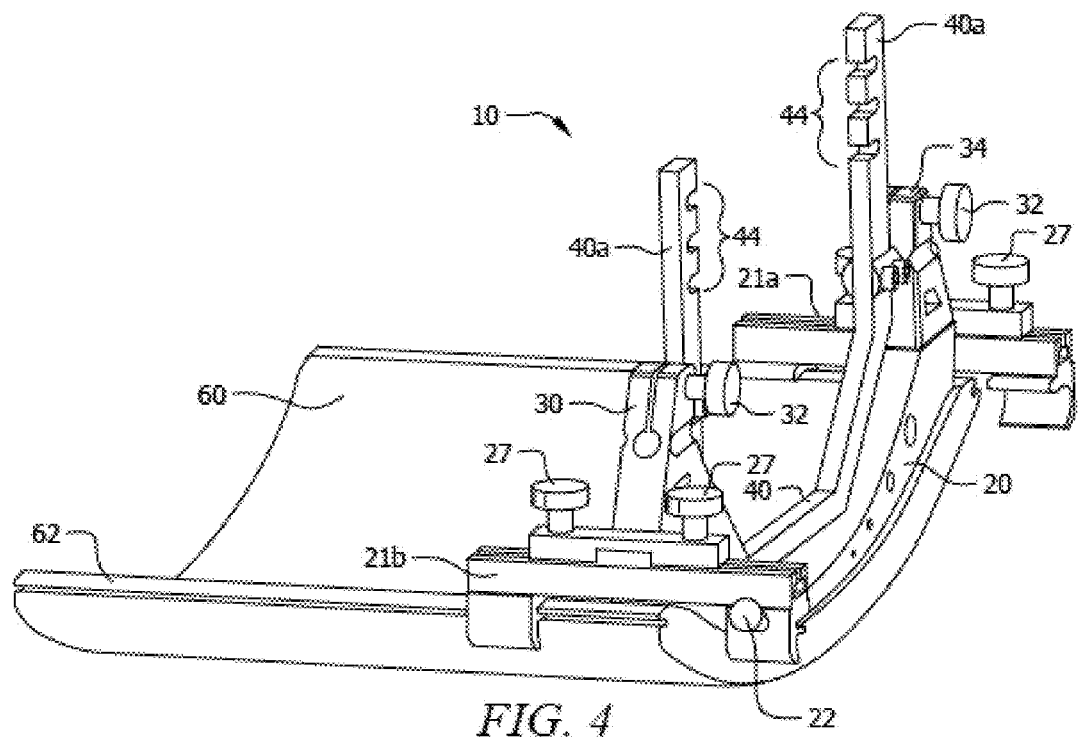
FIG. 4 is a perspective view of the front side of the imaging table-to-head frame adapter shown in FIG. 1, as viewed from the upper left of the front side of the device. The figure shows the imaging table-to-head frame adapter as it slides on to, and partially engages, a pair of grooves on either side of an imaging table. Note that the front attachment members on either side of the adapters are not engaged in this figure.
Figure 5:
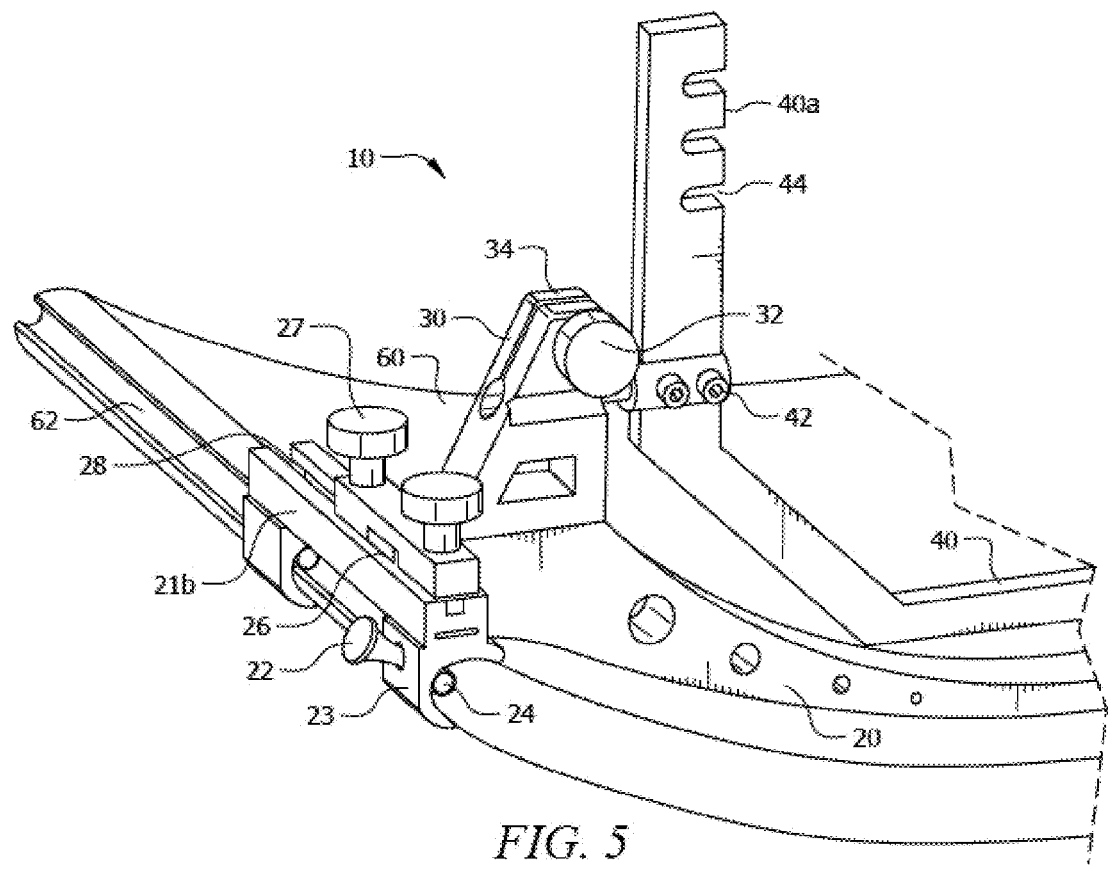
FIG. 5 is a perspective view of the outside left half of the front side of the imaging table-to-head frame adapter shown in FIG. 1. The figure shows the imaging table-to-head frame adapter after it has slid on to, and fully engaged, a of groove on a side of an imaging table.
Figure 6:
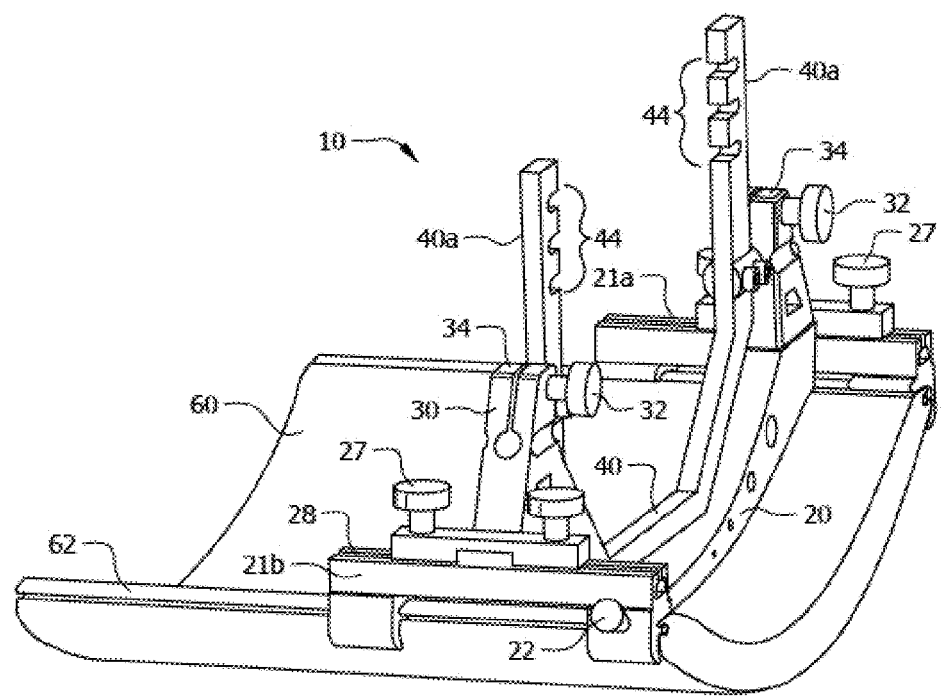
FIG. 6 is a perspective view of the front side of the imaging table-to-head frame adapter shown in FIG. 1, as viewed from the upper left of the front side of the device. The figure shows the imaging table-to-head frame adapter after it has slid on to, and fully engaged, a pair of grooves on either side of an imaging table.

FIG. 2 shows a perspective view of one of the table attachment members 21 in greater detail. A pair of downwardly extending, curved clamps 23a and 23b are located at each end of the table attachment member 21. The downwardly extending, curved clamps 23 wrap around distal sides of an imaging table, as shown in FIG. 5 (See also FIGS. 4 and 6). Referring again to FIG. 2, the table attachment members 21 includes a peg or key 24 that slots into and engages a respective groove formed within and extending along the imaging table in substantially parallel, spaced-apart relationship, as illustrated (see FIGS. 4-6 and FIG. 8 for the table grooves 62). The keys 24a and 24b of the table attachment member 21 are configured to matingly engage a respective groove/slot 62 in the imaging table 60. The keys 24 are shown as having a round shape, but they may have another configuration such as a trapezoidal or t-shape configuration. Each groove on the imaging table has a corresponding shape (e.g. round, trapezoidal or t-shaped) to mate with the key. Each table attachment member 21 has a pair of clamps 23a and 23b with a respective key (i.e. 24a and 24b, respectively). Key 24b is fixed with respect to clamp 23b, which results in the key 24b slidingly engaging the respective groove, but the key does not provide substantial resistance to movement along the length of the groove. In contrast, key 24a may be drawn towards (tightened) or away from (loosened) clamp 23a by turning knob 22. Tightening the key 24a to the clamp 23a results in the adapter 10 becoming affixed to, or locked into position on, an imaging table.

Embodiments of the present invention, however, are not limited to the illustrated base 20 and attachment member 21 configuration or to the illustrated engagement of attachment member 21 and imaging table 60. Furthermore, it is anticipated that an attachment member assembly of the present invention can be customized to fit and be secured to additional types of imaging tables. In other words, the attachment member assembly may be a universal assembly usable with several different imaging tables or systems from different manufacturers, or may be table-specific.

As discussed above, fore-aft movement along an imaging table, or at least attachment to an imaging table, is generally made possible using the clamp 23 and key 24 system of the table attachment member 21. FIGS. 4-6 and FIG. 8 show attachment of the adapter 10 to a table 60 having a groove 62 running the length of the table. In such a situation the fore/aft adjustment of the adapter could generally be made simply by using the clamp 23 and key 24 system of the table attachment member 21. Note that the phrase "fore/aft adjustment" refers to movement along the lengthwise aspect of a table. However, in some instances it might not possible to move an adapter 10 along the length of an imaging table. For example, the groove in the table might only be long enough to accommodate attachment of the adapter to the table, but not have additional length to supply proper fore/aft adjustment. The embodiment of the imaging table-to-head frame adapter shown in FIG. 1 has an additional mechanism for adjusting the fore/aft placement of the adapter, referred to herein as the fore/aft adjustment member 26.

Figure 18:
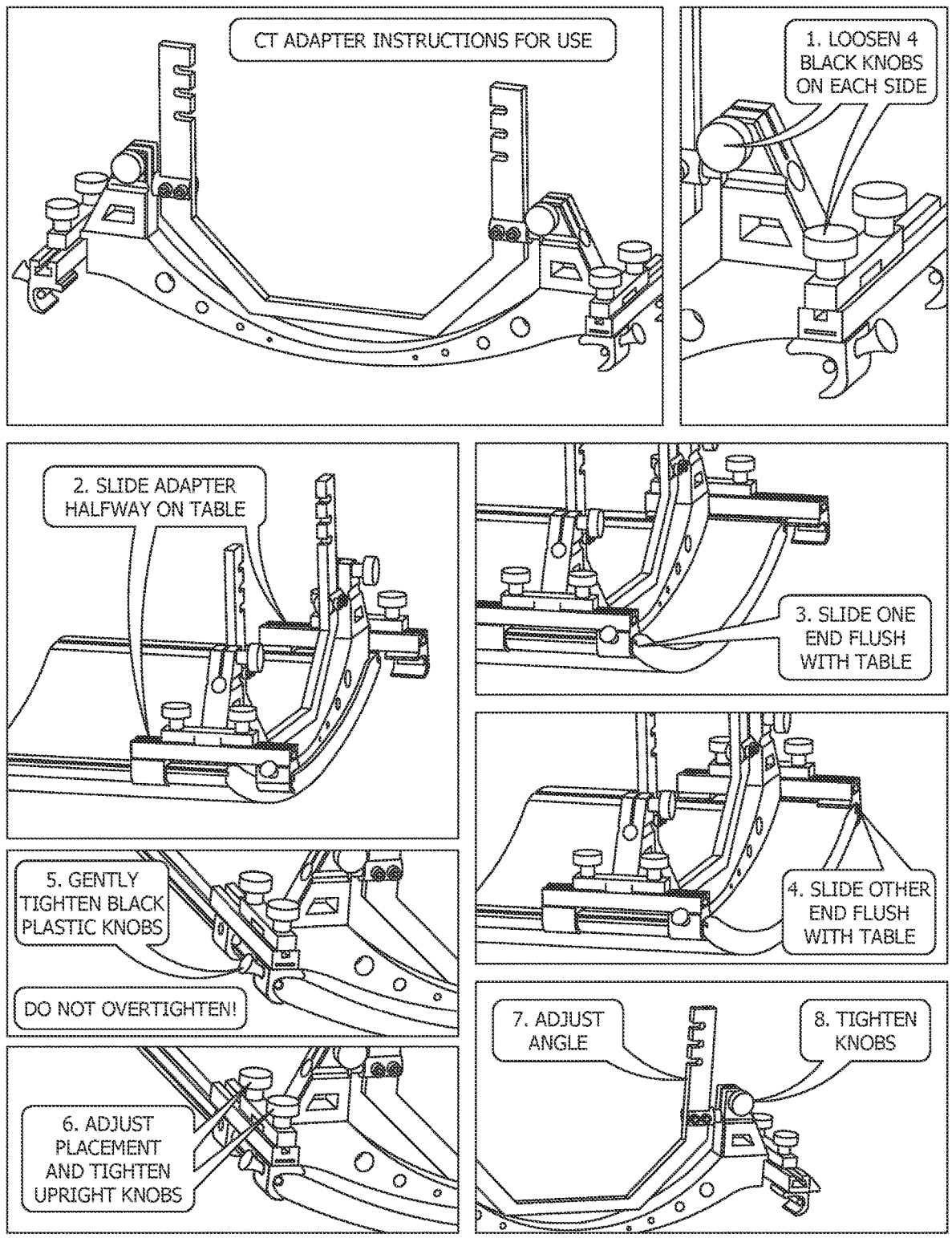
FIG. 18 is a series of images illustrating the mounting of the adapter on an imaging table and the adjustment of the imaging table-to-head frame adapter as in the embodiment shown in FIG. 1.
Figure 19:
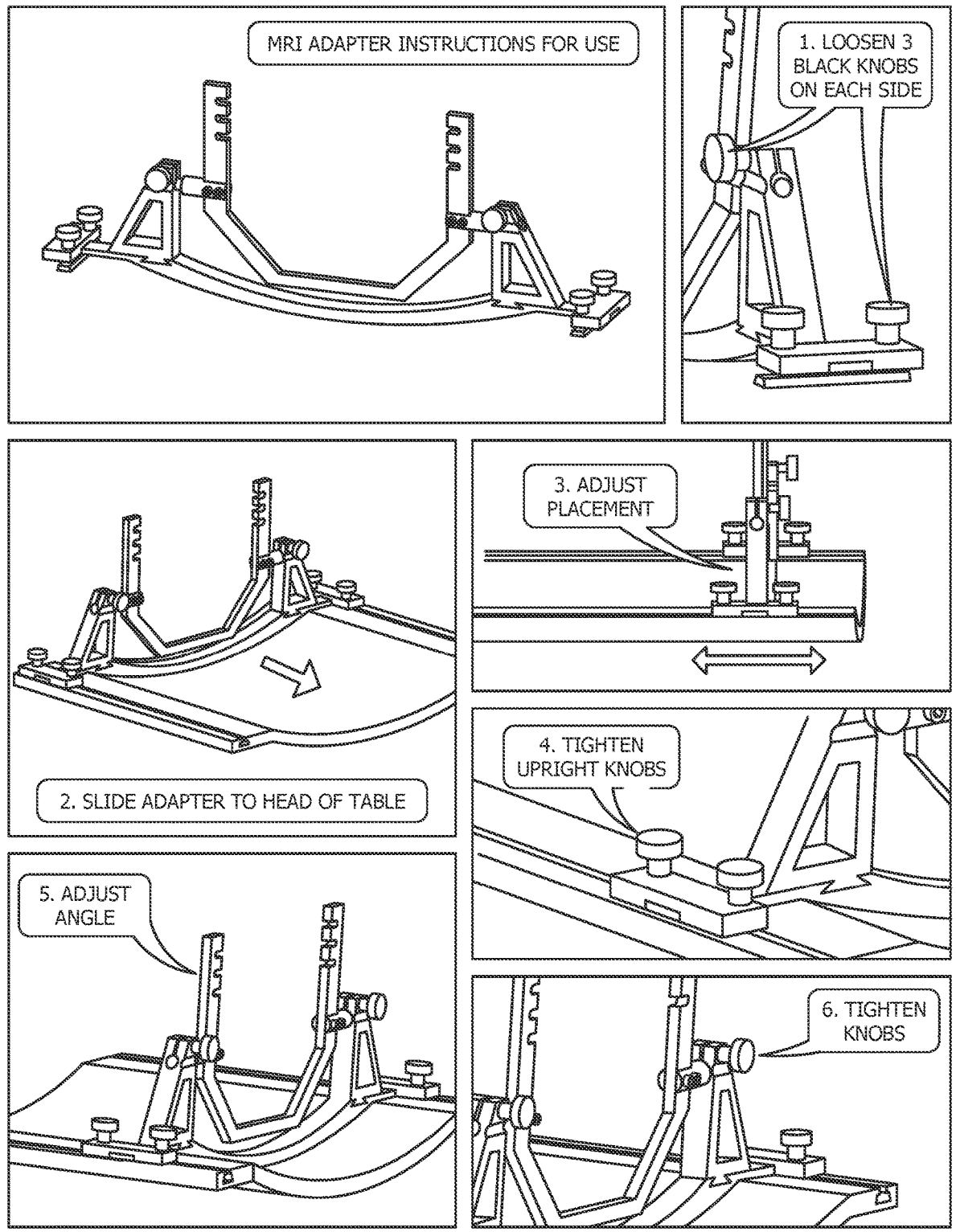
FIG. 19 is a series of images illustrating the mounting of the adapter on an imaging table and the adjustment of the imaging table-to-head frame adapter as in the embodiment shown in FIG. 9.

Referring to FIG. 2, the fore/aft adjustment member 26 includes a peg or key 29 (not shown) extending beneath the fore/aft adjustment member 26 that slots into and engages a respective groove 28 formed within and extending along the top of the table attachment member 21. The keys 29 of the fore/aft adjustment member 26 are configured to matingly engage a respective groove/slot 28 in the table attachment member 21. The groove 28 is shown as having a trapezoidal shape (e.g. see FIG. 3), but they may have another configuration such as around or t-shape configuration. The fore/aft adjustment member 26 is locked and unlocked by tightening and loosening knobs 27. For example, the knobs 27 would be loosened to allow movement of the upper portion of the adapter 10 to the desired position, while the lower portion of the adapter 10, namely the table attachment members 21 with its clamps 23 and keys 24, would remain affixed in their position on the table. Once the top portion of adapter 10 is situated in the desired fore/aft position, the knobs 27 would be tightened to secure the upper portion of the adapter 10 in that position. FIGS. 18 and 19 illustrate the stepwise adjustment of the adapter, including the positioning of an adapter on an imaging table. The embodiment shown in FIG. 18 includes fore/aft adjustment members on either side of the adapter's base, while the embodiment shown in FIG. 19 (as well as the embodiments shown in FIGS. 8-13) eliminates the fore/aft adjustment members. Consequently, the embodiment shown in FIGS. 9-17 must be adjusted/positioned along the length of an imaging table using only the clamp 23 and key 24 system of the table attachment member 21.

Figure 3:
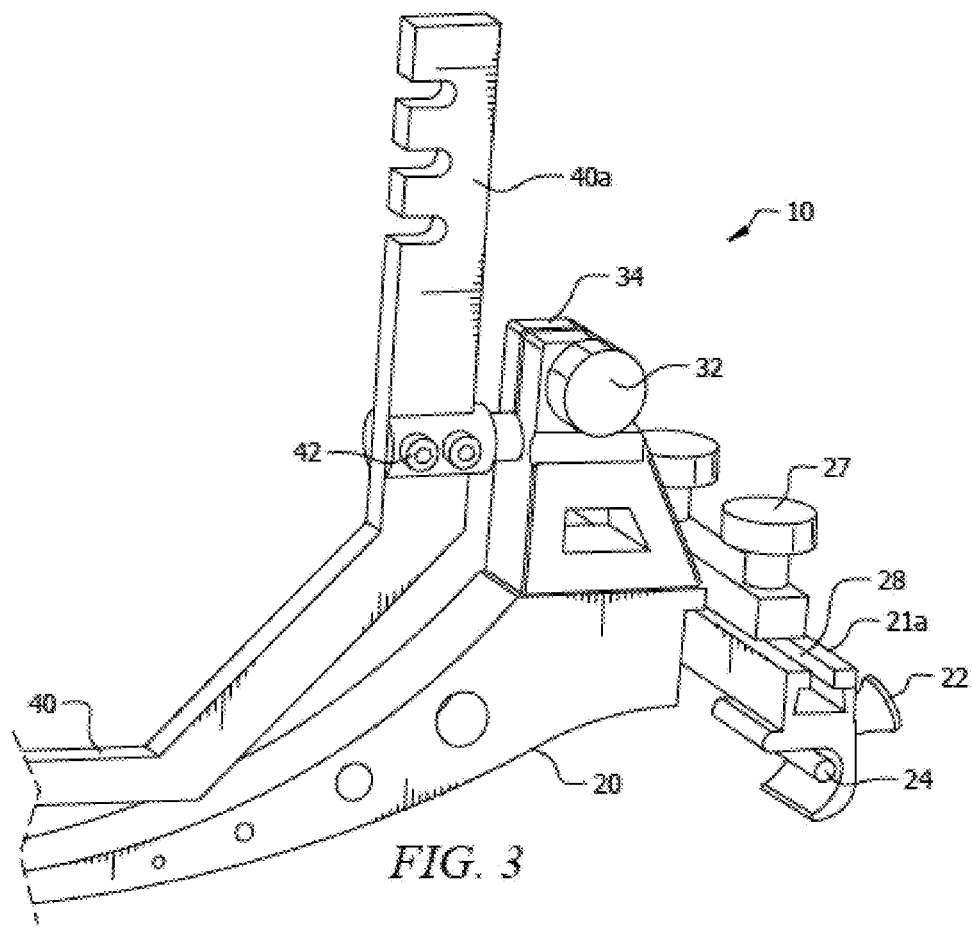
FIG. 3 is a perspective view of the inside right-half of the front side of the imaging table-to-head frame adapter shown in FIG. 1.
Figure 7:
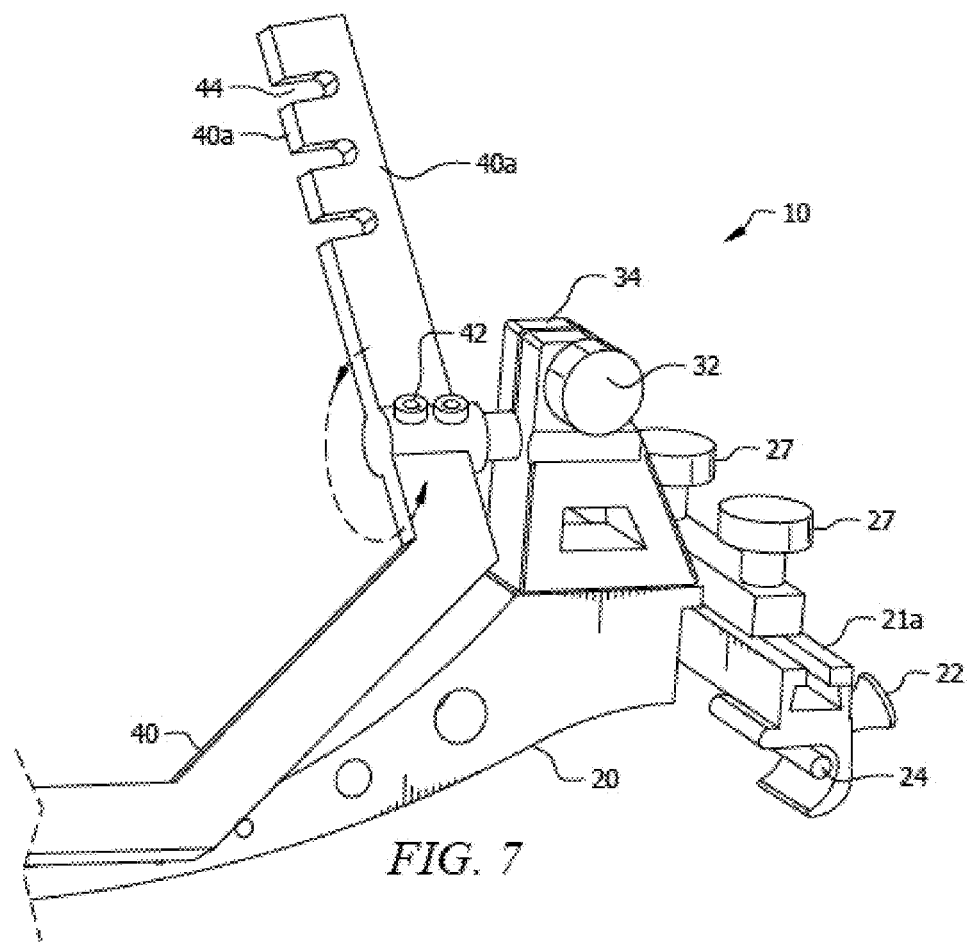
FIG. 7 is a perspective view of the inside right-half of the front side of the imaging table-to-head frame adapter shown in FIG. 1. The figure depicts the rotation of the frame relative to the base.
Figure 8:
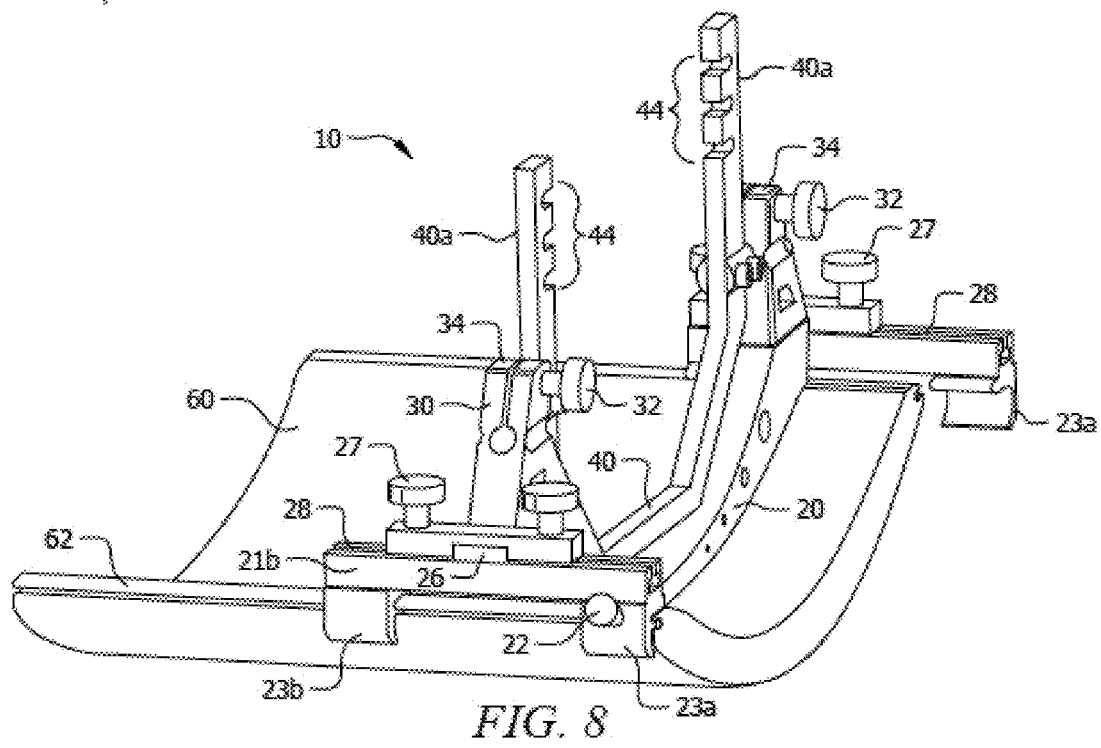
FIG. 8 is a perspective view of the front side of the imaging table-to-head frame adapter shown in FIG. 1, as viewed from the upper left of the first side of the device. The figure shows the imaging table-to-head frame adapter after the attachment member on the left side (or the side closest in the drawing) has slid on to, and fully engaged, the groove one side of an imaging table, while the attachment member in the right side (or the side farthest in the drawing) has only partially engaged the groove on the far side of the imaging table.
Figure 9:
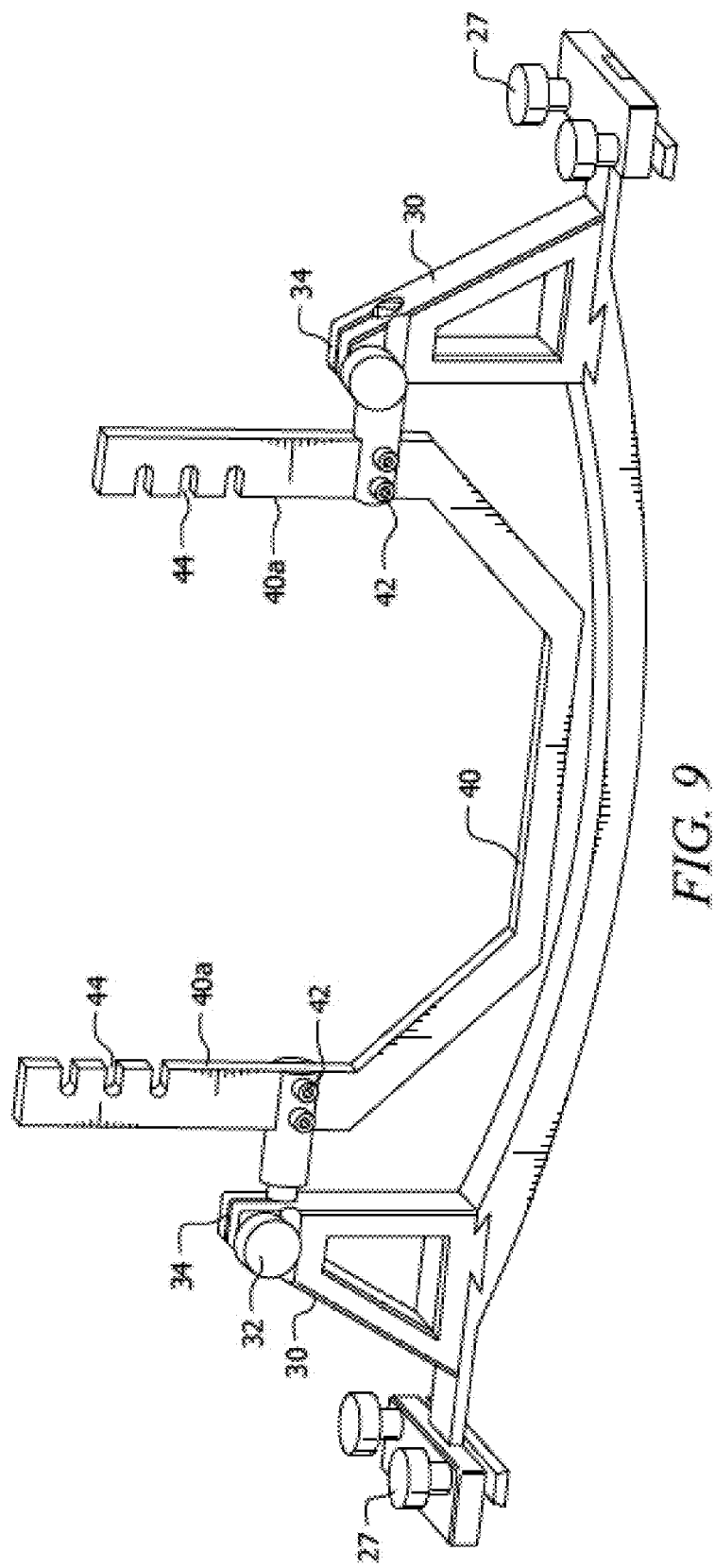
FIG. 9 is a perspective view of the front side of an alternative embodiment of an "imaging table-to-head frame adapter" according to some aspects of the present invention.
Figure 10:
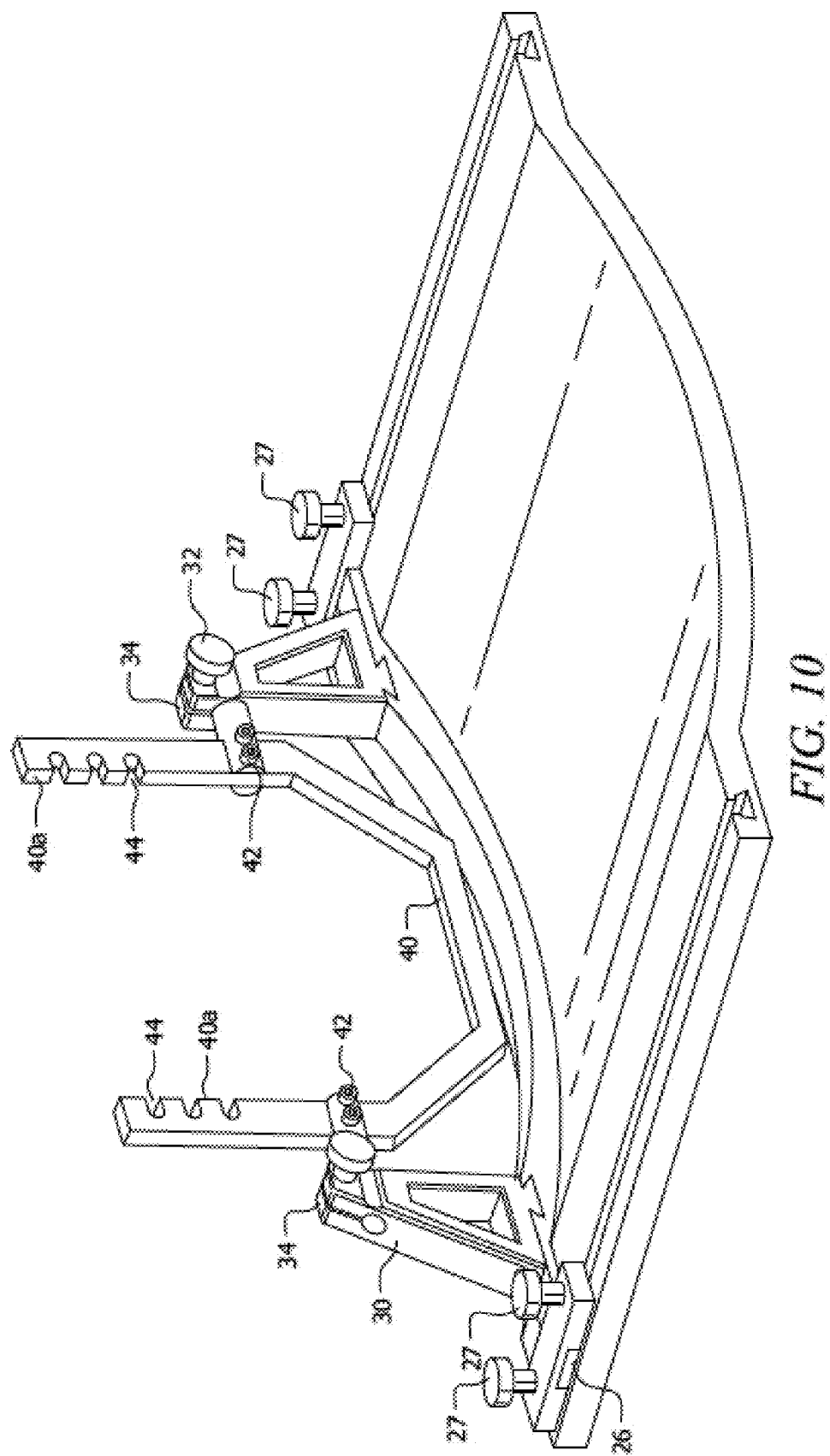
FIG. 10 is a perspective view of the front side of the "imaging table-to-head frame adapter" shown in FIG. 9. The figure shows the imaging table-to-head frame adapter affixed to an imaging table.

Returning to FIG. 1, the base 20 of the illustrated head fixation stabilizer 10 includes a pair of upwardly extending supports 30. The base 20 and upwardly extending supports 30 may be an integral unit, or may be separate components. In the illustrated embodiment, the upwardly extending supports 30 and base 20 are an integral unit. The upwardly extending supports 30 rotateabley engage the head fixation frame 40 using a pair of pivot members 42. The pivot members 42 are mounted on lateral sides of the head fixation frame 40 using any number of fasteners, including screws, rivets, pins, studs or adhesives. Extending outwardly from the point of attachment, the pivot member 42 includes a rod. The rod of the pivot member is received in a complementary cavity in the upwardly extending supports 30. A relief slot 34 (see FIG. 2) is located in the upwardly extending supports 30 immediately above the pivot member cavity. A bolt passes through the upwardly extending supports 30 to join the opposing portions of the supports on either end of the relief slot 34. The bolts are actuated by the support knobs 32, which relieve/expand or contract the opposing portions of the supports, thereby allowing or preventing rotation of the head fixation frame 40 within the upwardly extending supports 30. Thus, in operation the head fixation frame 40 can be rotated about a horizontal axis defined by the connection (i.e. pivot members 42) of the frame to the upwardly extending supports 30 to enable a head frame securing a subject's head to be properly oriented about that axis. FIG. 3 shows the head fixation frame 40 in a vertical orientation, while FIG. 7 show the same perspective view as shown in FIG. 3, but with the head fixation frame 40 rotated about the axis of the pivot member 42. Once the desired orientation is achieved (e.g. to ensure the proper orientation for imaging and/or patient comfort) the position is locked in place using the support knobs 32 so the subject cannot alter that parameter during the subsequent procedure.

Figure 25A:
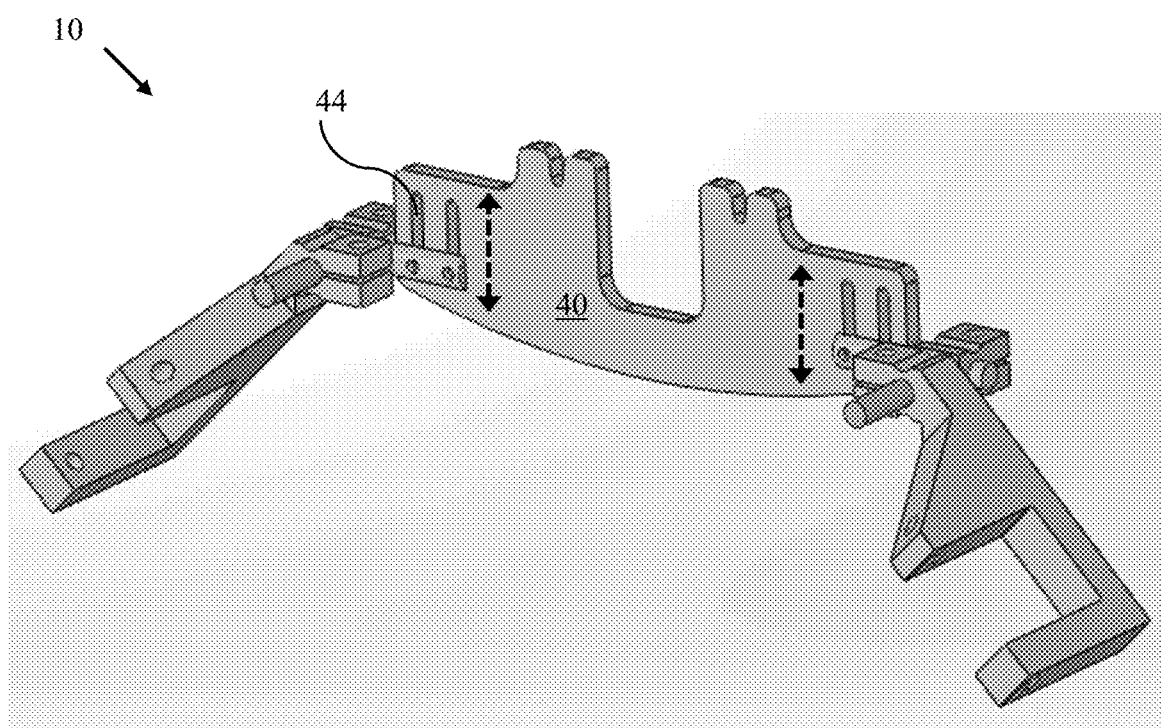
FIG. 25a is a front perspective view of the imaging table-to-head frame adapter shown in FIGS. 23a and 23b.
Figure 25B:
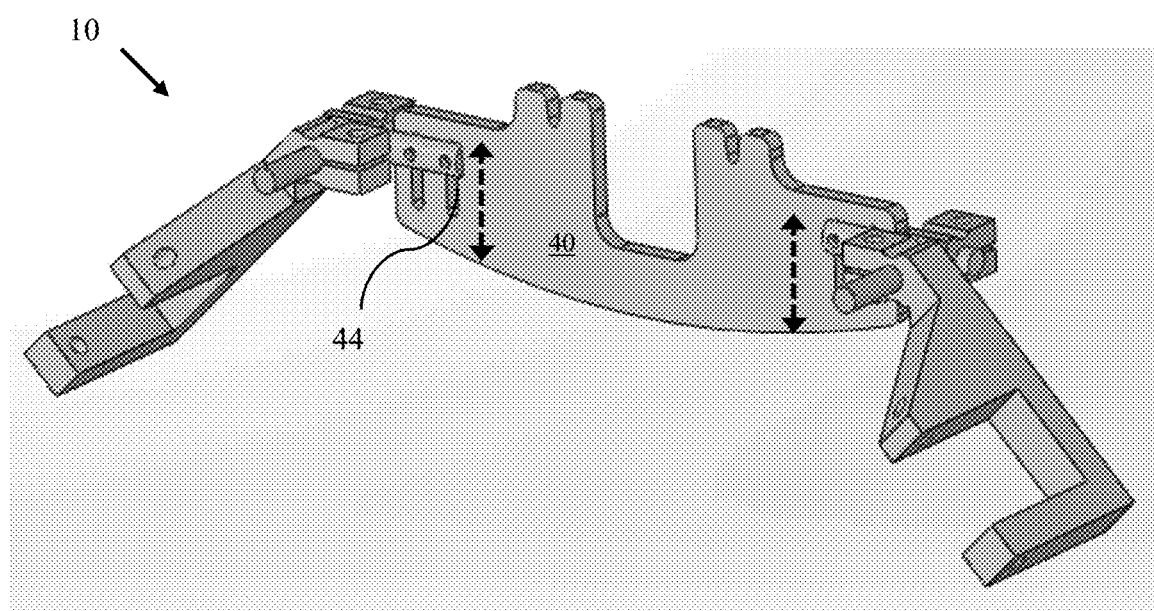
FIG. 25b is a front perspective view of the imaging table-to-head frame adapter shown in FIGS. 23a and 23b.

As shown in FIG. 1, the head fixation frame 40 includes a plurality (e.g. three) slots 44 adapted to receive fasteners to affix a head frame to the vertically extending arms 40a on the head fixation frame 40 of the head fixation stabilizer 10. Referring to FIG. 11, a head frame 70 generally affixes to the head fixation frame 40 using a pair of fasteners engaging a slot 44 on opposing vertically extending arms 40a on the head fixation frame 40. By having a plurality of vertically-spaced slots 44, the height at which a head frame is supported by the head fixation frame 40 can be adjusted to meet the needs of the particular application for a subject. Alternatively, slots can be employed, such as is shown in FIGS. 25a and 25b, to achieve nearly infinite adjustment with a range. Note that knobs 27 are omitted in FIGS. 11-13 for the purposes of illustration of other features, namely the affixed head frame.

Figure 20:
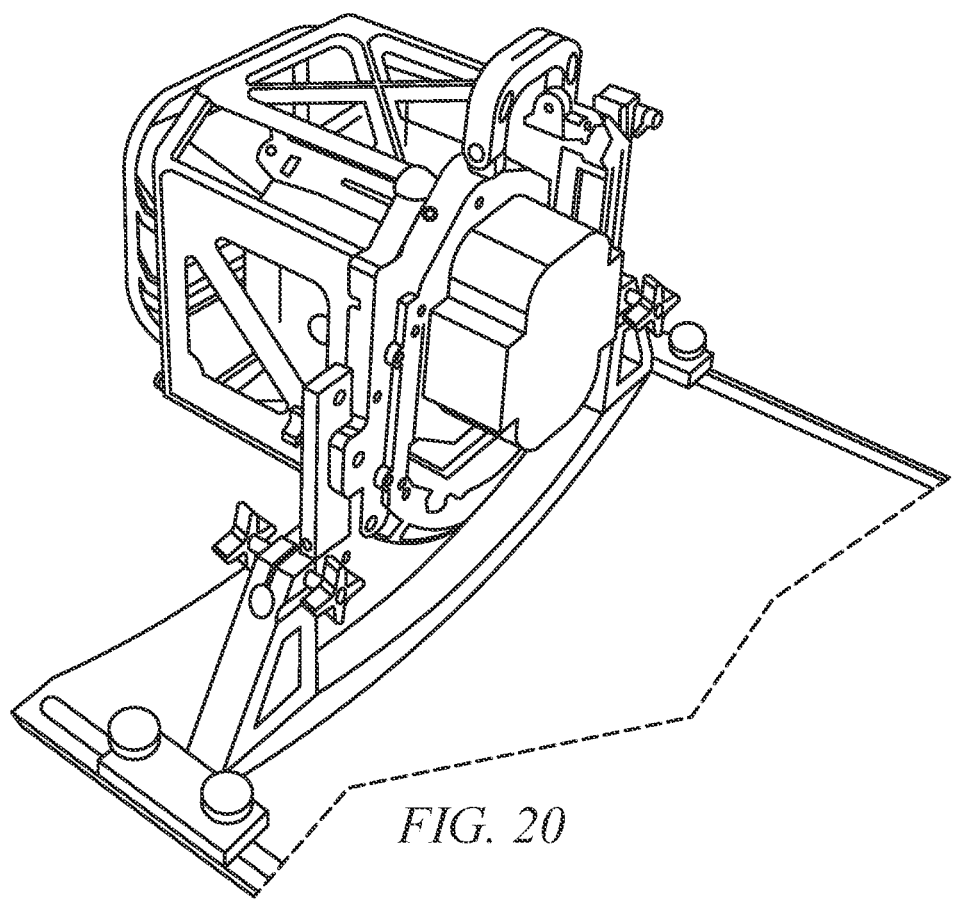
FIG. 20 is a photograph of an imaging table-to-head frame adapter affixed to an imaging table, with a head frame affixed to the table-to-head frame adapter and a phantom of a subject's head in the head frame.
Figure 21:
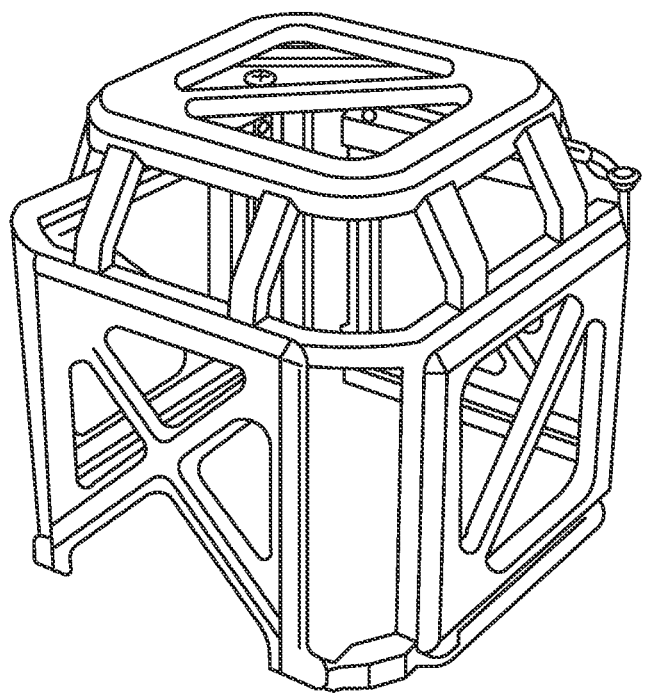
FIG. 21 is a perspective view of a Luminant™ MR/CT localizer frame, as produced by Integra LifeSciences Corporation of Plainsboro, N.J.
Figure 22:
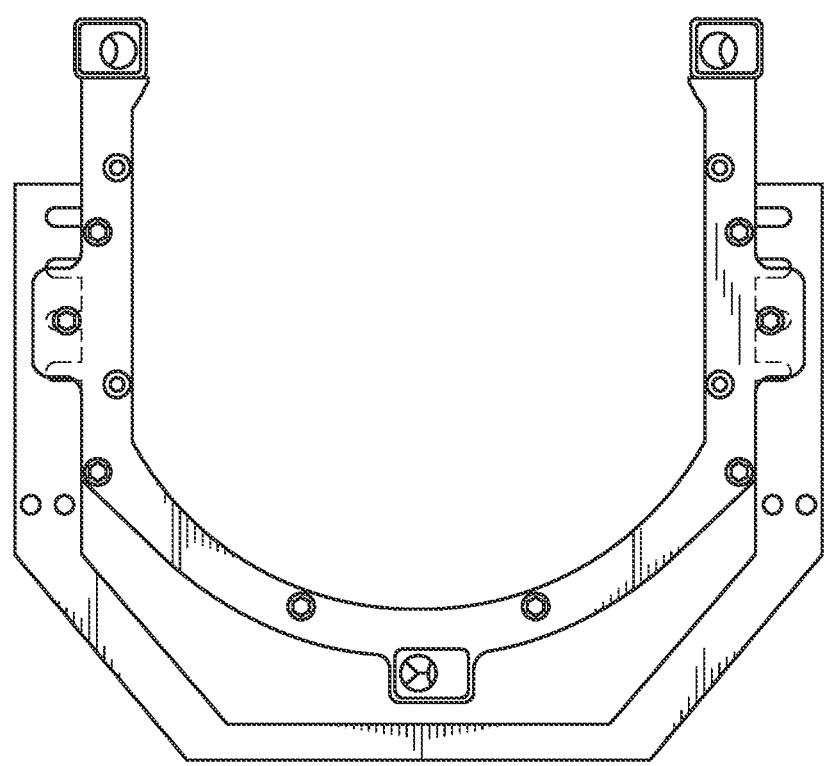
FIG. 22 is an image illustrating the frame of the adapter affixed to a head frame. The illustration shows a portion of the adapter (in darker gray) affixed to a portion of a head frame (in lighter gray).
Figure 23A:
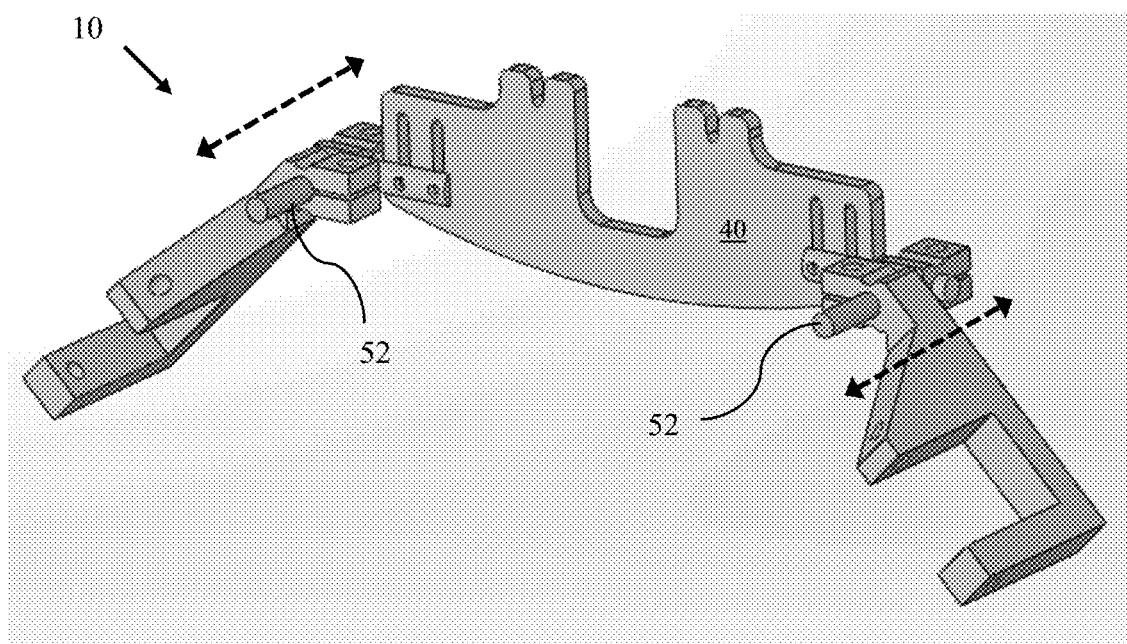
FIG. 23a is a front perspective view of an alternative embodiment of an imaging table-to-head frame adapter according to some aspects of the present invention.
Figure 23B:
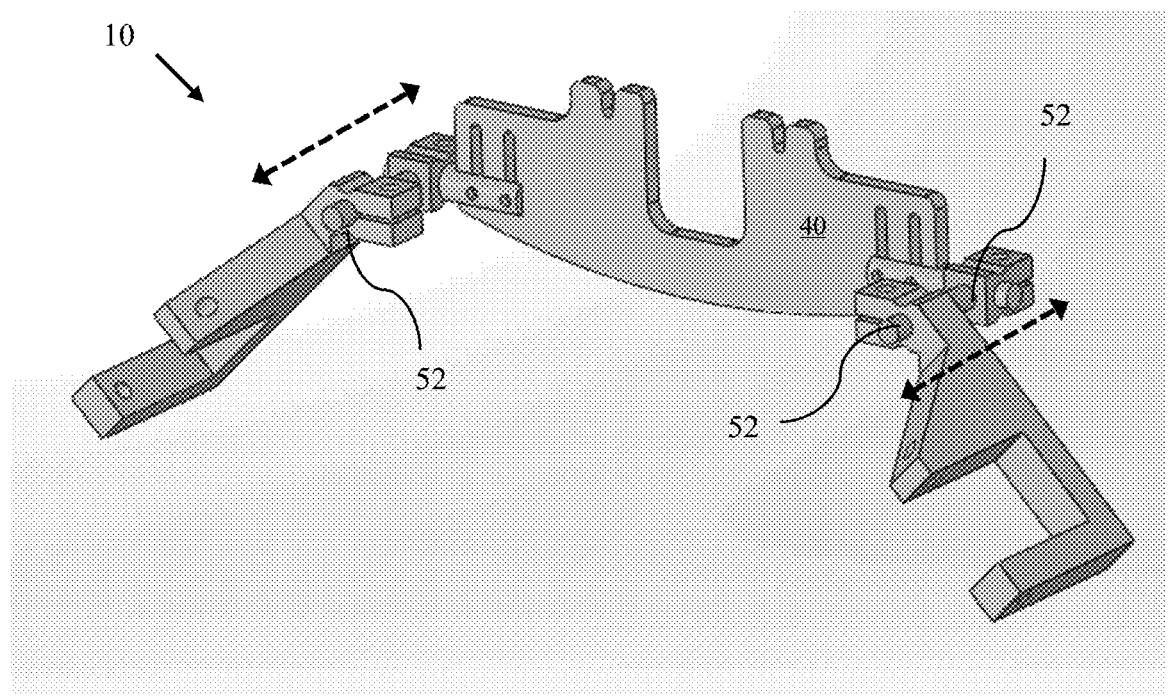
FIG. 23b is a front perspective view of an alternative embodiment of an imaging table-to-head frame adapter according to some aspects of the present invention.
Figure 24A:
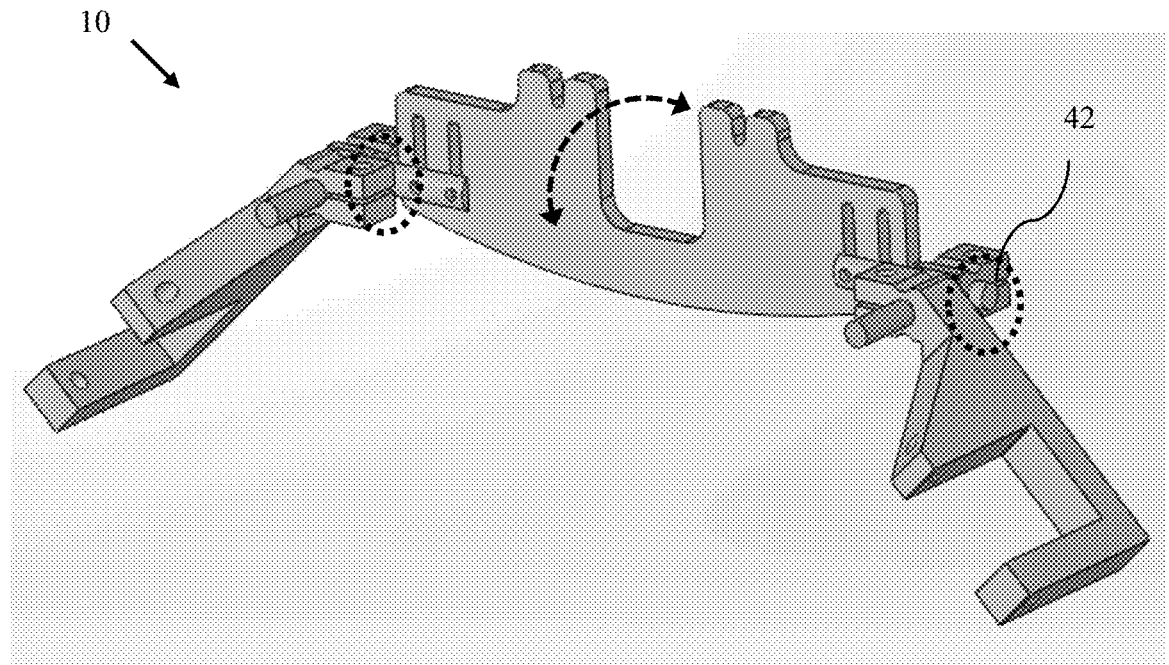
FIG. 24a is a front perspective view of the imaging table-to-head frame adapter shown in FIGS. 23a and 23b.
Figure 24B:
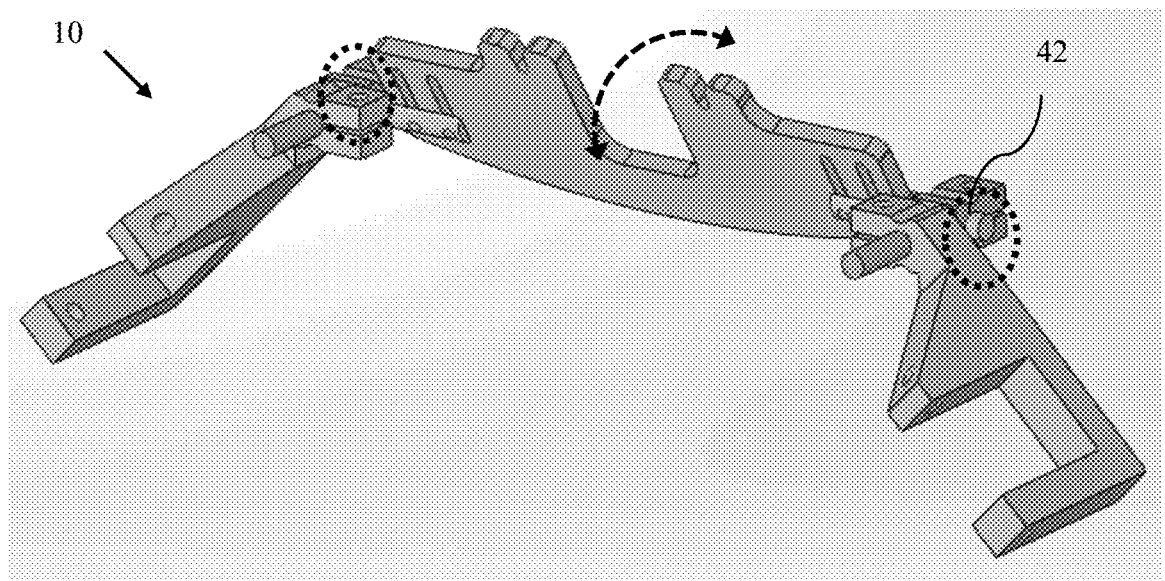
FIG. 24b is a front perspective view of the imaging table-to-head frame adapter shown in FIGS. 23a and 23b.

FIG. 20 shows the image table-to-head frame adapter affixed to an imaging table. Affixed to the image table-to-head frame adapter is an arc adapter plate from Integra LifeSciences Corporation. The arc adapter plate is shown in more detail in FIG. 22. Affixed to the arc adapter plate in FIG. 20 is a universal compact head ring subassembly and a Luminant™ MR/CT localizer frame. The Luminant™ MR/CT localizer frame is shown in more detail in FIG. 21. Integra LifeSciences has a line of CT clamps that can be used to mount their head frames to a variety of tables. However, these assemblies have numerous shortcomings. For example, the CT clamps from Integra cannot be rotated, which forces a subject's head into a position with no options to alter the angle. Also, the prior CT clamps do not provide for height adjustments. This inability to fine tune the position of the head frame can lead to great patient discomfort, especially when an imaging procedure may requires the subject to hold still for long periods of time. In short, prior systems force the tech to fit the patient to the device, not the device to the patient. This can take an enormous physical and emotional toll on a patient. The present invention overcomes these deficiencies by providing a modular system that can interface with a wide variety of head frames and tables, while offering an extensive range of adjustability. In addition, the added flexibility allows the practitioner to address the subject's positioning as may be required for a given scan.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. An imaging table-to-head frame stabilizer for holding the head of a patient in a selected position during a medical procedure, comprising:
    a base;
    an attachment member connected to the base to selectively affix the stabilizer to an imaging table;
    a pair of spaced-apart supports directly attached to or directly integrated with the base, the pair of spaced-apart supports extending upwardly from opposite halves of the base;
    a stabilizer frame rotatably attached to the pair of supports, the stabilizer frame having a plurality of attachment positions for a head frame used to secure the head of a subject during imaging, wherein the plurality of attachment positions enables a user to selectively set the head frame at different heights with respect to the stabilizer frame; and
    a locking mechanism to selectively prevent rotation of the stabilizer frame attached to the pair of supports.

2. The imaging table-to-head frame stabilizer according to claim 1, wherein the attachment positions for the head frame on the stabilizer frame are a plurality of slots configured to securely engage the head frame in a plurality of user selected locations on the frame thereby facilitating the height adjustment of the head frame.

3. The imaging table-to-head frame stabilizer according to claim 1, wherein the plurality of attachment positions on the stabilizer frame is adapted to accommodate a range of heights for the desired positioning of a subject for imaging as that subject rests upon an imaging table.

4. The imaging table-to-head frame stabilizer according to claim 1, wherein the attachments members are clamps that slidingly engage the imaging table, thereby allowing the imaging table-to-head frame stabilizer to be adjusted in a fore-aft direction along the table and locked thereto.

5. The imaging table-to-head frame stabilizer according to claim 1, wherein the attachments members are clamps.

6. The imaging table-to-head frame stabilizer according to claim 1, wherein the attachments members are adapted to affix the imaging table-to-head frame stabilizer to a table selected from the group consisting of a magnetic resonance imaging (MRI) table, a computed tomography (CT) imaging table, positron emission tomography (PET) imaging table, and an X-ray imaging table.

7. The imaging table-to-head frame stabilizer according to claim 1, further comprising a fore-aft adjustment member disposed between the attachment member and the base, wherein the fore-aft adjustment member facilitates positioning of the base relative to the attachment member.

8. The imaging table-to-head frame stabilizer according to claim 7, wherein the fore-aft adjustment member includes a first unit coupled to the attachment member and a second unit slidingly engaged to the first unit and coupled to the base and a locking mechanism connected to one of the units and adapted to selectively lock the fore-aft adjustment member.

9. An imaging table-to-head frame stabilizer for holding the head of a patient in a selected position during a medical procedure, comprising:
    a base;
    an attachment member connected to the base to affix the base to an imaging table;
    a pair of upwardly extending spaced-apart supports attached to the base, the supports being spaced apart in a lateral direction that is perpendicular to a longitudinal axis of the imaging table when the stabilizer is secured to the imaging table, wherein the longitudinal axis of the imaging table extends from a head end to a foot end of the imaging table;

a stabilizer frame rotatably attached to the pair of supports, the stabilizer frame having a plurality of attachment positions for a head frame used to secure the head of a subject during imaging, wherein the plurality of attachment positions enables a user to selectively set the head frame at different heights with respect to the stabilizer frame; and a locking mechanism to selectively prevent rotation of the stabilizer frame attached to the pair of supports.

10. The imaging table-to-head frame stabilizer according to claim 9, wherein the attachment positions for the head frame on the stabilizer frame are a plurality of slots configured to securely engage the head frame in a plurality of user selected locations on the frame thereby facilitating the height adjustment of the head frame.

11. The imaging table-to-head frame stabilizer according to claim 9, wherein the attachments members are adapted to affix the imaging table-to-head frame stabilizer to a table selected from the group consisting of a magnetic resonance imaging (MRI) table, a computed tomography (CT) imaging table, positron emission tomography (PET) imaging table, and an X-ray imaging table.

12. The imaging table-to-head frame stabilizer according to claim 9, further including a fore-aft adjustment member, wherein the fore-aft adjustment member includes a first unit coupled to the attachment member and a second unit slidingly engaged to the first unit and coupled to the base and a locking mechanism connected to one of the units and adapted to selectively lock the fore-aft adjustment member.

13. An imaging table-to-head frame stabilizer for holding the head of a patient during a medical procedure, comprising:

a pair of spaced-apart supports extending upwardly from opposite halves of a base, wherein the spaced-apart supports are directly attached to or directly integrated with the base;

a stabilizer frame rotatably and slidingly attached to the pair of supports, the stabilizer frame providing an attachment position for a head frame used to secure the head of a subject during imaging, whereby slidingly attaching the stabilizer frame to the supports enables a user to adjust the relative height of the head frame with respect to the stabilizer frame;

a locking mechanism to selectively prevent rotation of the stabilizer frame attached to the pair of supports;

a locking mechanism to selectively lock the height of the stabilizer frame slidingly attached to the pair of supports; and a locking mechanism to selectively adjust the horizontal disposition of the stabilizer frame with respect to the imaging table.

14. The imaging table-to-head frame stabilizer according to claim 13, further including a clamp to lock the imaging table-to-head frame stabilizer to an imaging table.

15. The imaging table-to-head frame stabilizer according to claim 14, wherein the clamp slidingly engages the imaging table, thereby allowing the imaging table-to-head frame stabilizer to be adjusted in a fore-aft direction along the table and locked thereto.

16. The imaging table-to-head frame stabilizer according to claim 14, wherein the clamp is adapted to affix the imaging table-to-head frame stabilizer to a table selected from the group consisting of a magnetic resonance imaging (MRI) table, a computed tomography (CT) imaging table, positron emission tomography (PET) imaging table, and an X-ray imaging table.

17. The imaging table-to-head frame stabilizer according to claim 14, further comprising a fore-aft adjustment member disposed between the clamp and the stabilizer frame, wherein the fore-aft adjustment member facilitates positioning of the stabilizer frame relative to the clamp.

18. An imaging table-to-head frame stabilizer for holding the head of a patient during a medical procedure, comprising:

a pair of upwardly extending spaced-apart supports, wherein the supports are spaced apart in a lateral direction that is perpendicular with respect to a longitudinal axis of the imaging table when the imaging table-to-head frame stabilizer is secured to the imaging table, wherein the longitudinal axis of the imaging table extends between a head end and a toe end of the imaging table;

a stabilizer frame rotatably attached to the pair of supports, the stabilizer frame providing a plurality of attachment positions for a head frame used to secure the head of a subject during imaging, wherein the plurality of attachment positions enables a user to selectively set the head frame at different heights with respect to the stabilizer frame;

a locking mechanism to selectively prevent rotation of the stabilizer frame attached to the pair of supports; and a locking mechanism to selectively adjust the horizontal disposition of the stabilizer frame with respect to the imaging table.

* * * * *